US010729860B1

(12) United States Patent
Boyer et al.

(10) Patent No.: US 10,729,860 B1
(45) Date of Patent: Aug. 4, 2020

(54) COMPUTERIZED ORAL PRESCRIPTION ADMINISTRATION FOR SECURELY DISPENSING A MEDICATION AND ASSOCIATED SYSTEMS AND METHODS

(71) Applicant: Berkshire Biomedical, LLC, Dallas, TX (US)

(72) Inventors: Robert Boyer, Dallas, TX (US); Christy Corey, Fishers, IN (US); Richard Cronenberg, Dallas, TX (US); John Kirkpatrick, Berthoud, CO (US)

(73) Assignee: BERKSHIRE BIOMEDICAL, LLC, Dallas, TX (US)

( * ) Notice: Subject to any disclaimer, the term of this patent is extended or adjusted under 35 U.S.C. 154(b) by 0 days.

(21) Appl. No.: 16/420,002

(22) Filed: May 22, 2019

(51) Int. Cl.
A61M 15/00 (2006.01)
G07C 9/25 (2020.01)

(52) U.S. Cl.
CPC .... A61M 15/0066 (2014.02); A61M 15/0021 (2014.02); A61M 15/0025 (2014.02); G07C 9/257 (2020.01); A61M 2205/13 (2013.01); A61M 2205/276 (2013.01); A61M 2205/3303 (2013.01); A61M 2205/3317 (2013.01);
(Continued)

(58) Field of Classification Search
CPC ............ A61M 15/006; A61M 15/0021; A61M 15/0025; A61M 2205/276; A61M 2205/3303; A61M 2205/3317; A61M 2205/50; A61M 2205/6009; A61M 2005/609; G07C 9/00087
See application file for complete search history.

(56) References Cited

U.S. PATENT DOCUMENTS 4,116,195 A 9/1978 James
4,237,884 A 12/1980 Erickson et al.
4,353,365 A 10/1982 Hallworth et al.
(Continued)

FOREIGN PATENT DOCUMENTS

DE 102014114601 A1 4/2016
KR 101221415 B1 1/2013
(Continued)

OTHER PUBLICATIONS

International Search Report issued in PCT/US2019/022287 dated Jul. 16, 2019.
(Continued)

Primary Examiner — Brandy S Lee
(74) Attorney, Agent, or Firm — Haynes and Boone, LLP

(57) ABSTRACT

In one embodiment, a member for securely dispensing a substance to an intended user includes a first member configured to threadedly engage with a housing containing the substance; a second member coupled to the first member, the second member configured to fixedly secure the first member to the housing; a third member including a cavity sized and shaped to selectively receive the second member; and a valve coupled to the first member such that: when the second member is received within the cavity, the valve is in an open state that allows the substance to be dispensed from the housing to the intended user in response to a processor determining that a unique biometric attribute of the intended user is detected, and when the second member is not received within the cavity, the valve is in a closed state that prevents the substance from being dispensed from the housing.

30 Claims, 24 Drawing Sheets

(52) U.S. Cl.
CPC ... *A61M 2205/50* (2013.01); *A61M 2205/609* (2013.01); *A61M 2205/6009* (2013.01)

(56) References Cited

U.S. PATENT DOCUMENTS

| | | | |
|---|---|---|---|
| 4,428,502 A | 1/1984 | Veltri |
| 4,474,308 A | 10/1984 | Bergeron |
| 4,717,042 A | 1/1988 | McLaughlin |
| 4,784,288 A | 11/1988 | Jennings |
| 5,159,581 A | 10/1992 | Agans |
| 5,583,831 A | 12/1996 | Churchill et al. |
| 5,791,515 A | 8/1998 | Khan et al. |
| 5,852,590 A | 12/1998 | de la Huerga |
| H0001782 H | 2/1999 | Wicks et al. |
| 5,881,721 A | 3/1999 | Bunce et al. |
| 5,947,329 A | 9/1999 | Bailey |
| 5,960,085 A | 9/1999 | de la Huerga |
| 5,971,594 A | 10/1999 | Sahai et al. |
| 5,990,782 A | 11/1999 | Lee |
| 6,018,289 A | 1/2000 | Sekura et al. |
| 6,032,155 A | 2/2000 | de la Huerga |
| 6,082,363 A | 7/2000 | Washburn |
| 6,089,864 A | 7/2000 | Buckner et al. |
| 6,112,942 A | 9/2000 | Deacon |
| 6,119,684 A | 9/2000 | Nohl et al. |
| 6,145,697 A | 11/2000 | Gudish |
| 6,163,736 A | 12/2000 | Halfacre |
| 6,198,383 B1 | 3/2001 | Sekura et al. |
| 6,259,654 B1 | 7/2001 | de la Huerga |
| 6,304,797 B1 | 10/2001 | Shusterman |
| 6,332,100 B1 | 12/2001 | Sahai et al. |
| 6,335,907 B1 | 1/2002 | Momich et al. |
| 6,408,330 B1 | 6/2002 | DeLaHuerga |
| 6,431,399 B2 | 8/2002 | Gabel et al. |
| 6,529,446 B1 | 3/2003 | de la Huerga |
| 6,604,650 B2 | 8/2003 | Sagar |
| 6,611,733 B1 | 8/2003 | De La Huerga |
| 6,702,146 B2 | 3/2004 | Varis |
| 6,779,024 B2 | 8/2004 | DeLaHuerga |
| 6,834,775 B1 | 12/2004 | Collins |
| 6,958,691 B1 | 10/2005 | Anderson et al. |
| 6,988,634 B2 | 1/2006 | Varis |
| 7,006,894 B2 | 2/2006 | de la Huerga |
| 7,042,807 B1 | 5/2006 | Breen |
| 7,048,141 B2 | 5/2006 | Abdulhay et al. |
| 7,061,831 B2 | 6/2006 | De La Huerga |
| 7,072,738 B2 | 7/2006 | Bonney et al. |
| 7,073,685 B1 | 7/2006 | Giraud et al. |
| 7,100,797 B2 | 9/2006 | Kahn et al. |
| 7,104,417 B2 | 9/2006 | Hilliard |
| 7,128,240 B1 | 10/2006 | Oesch |
| 7,147,127 B2 | 12/2006 | Lepke et al. |
| 7,178,688 B2 | 2/2007 | Naufel et al. |
| 7,182,955 B2 | 2/2007 | Hart et al. |
| 7,213,721 B2 | 5/2007 | Abdulhay et al. |
| 7,216,802 B1 | 5/2007 | De La Huerga |
| 7,269,476 B2 | 9/2007 | Ratnakar |
| 7,295,890 B2 | 11/2007 | Jean-Pierre |
| 7,302,311 B2 | 11/2007 | Varis |
| 7,328,859 B2 | 2/2008 | Hornsby et al. |
| 7,359,765 B2 | 4/2008 | Varvarelis et al. |
| 7,366,675 B1 | 4/2008 | Walker et al. |
| 7,392,918 B2 | 7/2008 | Holloway et al. |
| 7,404,500 B2 | 7/2008 | Marteau et al. |
| 7,648,093 B2 | 1/2010 | Kruger |
| 7,711,449 B2 | 5/2010 | Abdulhay et al. |
| 7,715,277 B2 | 5/2010 | de la Huerga |
| 7,719,927 B1 | 5/2010 | Robinson et al. |
| 7,801,745 B2 | 9/2010 | Walker et al. |
| 7,810,673 B2 | 10/2010 | Laucesseur et al. |
| 7,831,336 B2 | 11/2010 | Gumpert |
| 7,844,361 B2 | 11/2010 | Jean-Pierre |
| 7,885,725 B2 | 2/2011 | Dunn |
| 7,941,534 B2 | 5/2011 | de la Huerga |
| 7,978,564 B2 | 7/2011 | De La Huerga |
| 7,988,016 B2 | 8/2011 | Klein et al. |
| 7,996,106 B2 | 8/2011 | Ervin |
| 8,019,471 B2 | 9/2011 | Bogash et al. |
| 8,028,856 B2 | 10/2011 | Erclelyi et al. |
| 8,029,538 B2 | 10/2011 | Burroughs et al. |
| 8,033,422 B2 | 10/2011 | Estrada |
| 8,055,509 B1 | 11/2011 | Walker et al. |
| 8,062,248 B2 | 11/2011 | Kindel |
| 8,069,056 B2 | 11/2011 | Walker et al. |
| 8,135,497 B2 | 3/2012 | Joslyn |
| 8,195,330 B2 | 6/2012 | Coe |
| 8,212,677 B2 | 7/2012 | Ferguson |
| 8,226,978 B2 | 7/2012 | Palmer et al. |
| 8,269,613 B2 | 9/2012 | Lazar |
| 8,279,076 B2 | 10/2012 | Johnson |
| 8,284,068 B2 | 10/2012 | Johnson |
| 8,319,613 B2 | 11/2012 | Lazar |
| 8,326,455 B2 | 12/2012 | Dunn |
| 8,357,114 B2 | 1/2013 | Poutiatine et al. |
| 8,391,104 B2 | 3/2013 | de la Huerga |
| 8,392,020 B2 | 3/2013 | Terzini |
| 8,417,378 B2 | 4/2013 | Joslyn |
| 8,483,872 B2 | 7/2013 | Ratnakar |
| 8,499,966 B2 | 8/2013 | Palmer et al. |
| 8,502,671 B2 | 8/2013 | Marcovici |
| 8,502,692 B2 | 8/2013 | Johnson |
| 8,511,478 B2 | 8/2013 | Terzini |
| 8,548,623 B2 | 10/2013 | Poutiatine et al. |
| 8,552,868 B1 | 10/2013 | Ferguson |
| 8,574,189 B2 | 11/2013 | Poutiatine et al. |
| 8,600,548 B2 | 12/2013 | Bossi et al. |
| 8,636,172 B2 | 1/2014 | Dunn |
| 8,666,539 B2 | 3/2014 | Ervin |
| 8,666,543 B2 | 3/2014 | MacVittie et al. |
| 8,669,863 B2 | 3/2014 | Alhuwaishel |
| 8,670,865 B2 | 3/2014 | Coe |
| 8,725,291 B2 | 5/2014 | Czaja et al. |
| 8,727,180 B2 | 5/2014 | Zonana et al. |
| 8,734,061 B2 | 5/2014 | Terzini |
| 8,753,308 B2 | 6/2014 | Palmer et al. |
| 8,778,393 B2 | 7/2014 | Palmer et al. |
| 8,807,131 B1 | 8/2014 | Tunnell et al. |
| 8,821,454 B2 | 9/2014 | Kriesel et al. |
| 8,854,225 B2 | 10/2014 | Johnson |
| 8,874,260 B2 | 10/2014 | Saltsov |
| 8,905,964 B2 | 12/2014 | Poutiatine et al. |
| 8,922,367 B2 | 12/2014 | Denny et al. |
| 8,973,338 B2 | 3/2015 | Terzini |
| 8,976,036 B2 | 3/2015 | Johnson |
| 8,985,388 B2 | 3/2015 | Ratnakar |
| 9,010,584 B2 * | 4/2015 | Law ................. B05B 11/0027 222/256 |
| 9,014,847 B2 | 4/2015 | Dunn |
| 9,019,097 B2 | 4/2015 | Choi et al. |
| 9,037,291 B2 | 5/2015 | Terzini |
| 9,043,015 B2 | 5/2015 | Ratnakar |
| 9,066,847 B2 | 6/2015 | Poutiatine et al. |
| 9,066,849 B2 | 6/2015 | Fung et al. |
| 9,155,682 B2 | 10/2015 | Boyd |
| 9,161,885 B1 | 10/2015 | Zhou |
| 9,211,559 B2 | 12/2015 | Law et al. |
| 9,218,458 B2 | 12/2015 | Baarman et al. |
| 9,235,689 B2 | 1/2016 | Ervin |
| 9,283,363 B1 | 3/2016 | Scorzelli et al. |
| 9,289,583 B2 | 3/2016 | Palmer et al. |
| 9,346,068 B2 | 5/2016 | Knight et al. |
| 9,361,772 B2 | 6/2016 | Johnson |
| 9,381,139 B2 | 7/2016 | Fung et al. |
| 9,414,899 B2 | 8/2016 | Altounian |
| 9,418,207 B1 | 8/2016 | Patton et al. |
| 9,436,298 B2 | 9/2016 | Draper et al. |
| 9,566,402 B2 | 2/2017 | Djupesland |
| 9,636,195 B2 | 5/2017 | Wolpo |
| 9,731,103 B1 | 8/2017 | Rouse et al. |
| 9,795,296 B2 | 10/2017 | Imran |
| 9,839,500 B2 | 12/2017 | Flyash et al. |
| 9,968,777 B1 | 5/2018 | Demarest et al. |
| 2001/0009398 A1 | 7/2001 | Sekura et al. |
| 2001/0022758 A1 | 9/2001 | Howard |

(56) References Cited

U.S. PATENT DOCUMENTS

| | | |
|---|---|---|
| 2003/0174554 A1 | 9/2003 | Dunstone et al. |
| 2004/0008123 A1 | 1/2004 | Carrender et al. |
| 2004/0117062 A1 | 6/2004 | Bonney et al. |
| 2004/0158349 A1 | 8/2004 | Bonney et al. |
| 2005/0230409 A1 | 10/2005 | von Schuckmann |
| 2006/0138162 A1 | 6/2006 | Anderson et al. |
| 2006/0166157 A1 | 7/2006 | Rahman et al. |
| 2006/0184271 A1 | 8/2006 | Loveless |
| 2006/0213921 A1 | 9/2006 | Abdulhay et al. |
| 2006/0218015 A1 | 9/2006 | Walker et al. |
| 2006/0282010 A1 | 12/2006 | Martin |
| 2007/0075842 A1 | 4/2007 | Russell et al. |
| 2007/0093932 A1 | 4/2007 | Abdulhay et al. |
| 2007/0095851 A1 | 5/2007 | Anderson et al. |
| 2007/0135790 A1 | 6/2007 | Auerbach |
| 2007/0138195 A1 | 6/2007 | Anderson et al. |
| 2007/0145065 A1 | 6/2007 | Anderson et al. |
| 2007/0170199 A1 | 7/2007 | York |
| 2007/0228065 A1 | 10/2007 | Anderson et al. |
| 2007/0261985 A1 | 11/2007 | Allen |
| 2007/0271001 A1 | 11/2007 | Ratnakar |
| 2008/0017658 A1 | 1/2008 | Wright |
| 2008/0027291 A1 | 1/2008 | Williams-Hartman |
| 2008/0027579 A1 | 1/2008 | van der Hoop |
| 2008/0054008 A1 | 3/2008 | Wright |
| 2008/0059228 A1 | 3/2008 | Bossi et al. |
| 2008/0140250 A1 | 6/2008 | Dave |
| 2008/0251530 A1 | 10/2008 | Holloway et al. |
| 2008/0283542 A1 | 11/2008 | Lanka et al. |
| 2009/0127157 A1 | 5/2009 | Costa et al. |
| 2009/0208898 A1 | 8/2009 | Kaplan |
| 2009/0210032 A1 | 8/2009 | Beiski et al. |
| 2009/0223994 A1 | 9/2009 | Getz |
| 2009/0277461 A1 | 11/2009 | Gallagher, Jr. |
| 2009/0277921 A1 | 11/2009 | Angelucci et al. |
| 2010/0006589 A1 | 1/2010 | Klein |
| 2010/0096399 A1 | 4/2010 | Ratnakar |
| 2010/0100237 A1 | 4/2010 | Ratnakar |
| 2010/0185456 A1 | 7/2010 | Kansal |
| 2010/0318218 A1 | 12/2010 | Muncy, Jr. et al. |
| 2010/0332023 A1 | 12/2010 | Tripathi et al. |
| 2011/0011883 A1 | 1/2011 | Nakkouri |
| 2011/0021983 A1 | 1/2011 | Jurson |
| 2011/0027746 A1 | 2/2011 | McDonough |
| 2011/0060455 A1 | 3/2011 | Bogash et al. |
| 2011/0060457 A1 | 3/2011 | De Vrught et al. |
| 2011/0142554 A1 | 6/2011 | Terzini |
| 2011/0146835 A1 | 6/2011 | Terzini |
| 2011/0160901 A1 | 6/2011 | Abrams, Jr. et al. |
| 2011/0202174 A1 | 8/2011 | Bogash et al. |
| 2011/0259910 A1 | 10/2011 | Knudsen |
| 2011/0295416 A1 | 12/2011 | Aquilonius et al. |
| 2011/0307592 A1 | 12/2011 | de la Huerga |
| 2012/0055948 A1 | 3/2012 | Leifeld et al. |
| 2012/0160716 A1 | 6/2012 | Chan et al. |
| 2012/0165975 A1 | 6/2012 | Yi et al. |
| 2012/0289905 A1 | 11/2012 | Julian et al. |
| 2013/0025607 A1 | 1/2013 | Altounian |
| 2013/0088328 A1 | 4/2013 | DiMartino et al. |
| 2013/0116818 A1 | 5/2013 | Hamilton |
| 2013/0120115 A1 | 5/2013 | Valls Chaparro et al. |
| 2013/0165828 A1 | 6/2013 | Sullivan |
| 2013/0168405 A1 | 7/2013 | Yuyama et al. |
| 2013/0211270 A1 | 8/2013 | St. Laurent et al. |
| 2013/0253286 A1 | 9/2013 | Fridman |
| 2013/0256331 A1 | 10/2013 | Giraud et al. |
| 2013/0280671 A1 | 10/2013 | Brawn et al. |
| 2013/0304255 A1 | 11/2013 | Ratnakar |
| 2013/0345859 A1 | 12/2013 | Omura et al. |
| 2014/0031975 A1 | 1/2014 | Poutiatine et al. |
| 2014/0046676 A1 | 2/2014 | Kibler et al. |
| 2014/0072932 A1 | 3/2014 | Brawn |
| 2014/0074283 A1 | 3/2014 | Blackburn |
| 2014/0114472 A1 | 4/2014 | Bossi et al. |
| 2014/0195043 A1 | 7/2014 | Ervin |
| 2014/0203021 A1 | 7/2014 | Zill |
| 2014/0207278 A1 | 7/2014 | Czaja et al. |
| 2014/0263423 A1 | 9/2014 | Akdogan et al. |
| 2014/0263425 A1 | 9/2014 | Akdogan et al. |
| 2014/0267719 A1 | 9/2014 | Akdogan et al. |
| 2014/0277705 A1 | 9/2014 | Czaja et al. |
| 2014/0277707 A1 | 9/2014 | Akdogan et al. |
| 2014/0277710 A1 | 9/2014 | Akdogan et al. |
| 2014/0278508 A1 | 9/2014 | Akdogan et al. |
| 2014/0278510 A1 | 9/2014 | McLean et al. |
| 2014/0303989 A1 | 10/2014 | Ferguson |
| 2014/0305963 A1 | 10/2014 | Zonana et al. |
| 2014/0316799 A1 | 10/2014 | Cosgrove et al. |
| 2014/0324216 A1 | 10/2014 | Beg et al. |
| 2014/0326744 A1 | 11/2014 | Ratnakar |
| 2014/0339248 A1 | 11/2014 | Reddy et al. |
| 2014/0339249 A1 | 11/2014 | Reddy et al. |
| 2014/0346184 A1 | 11/2014 | Bae et al. |
| 2014/0346186 A1 | 11/2014 | Reddy et al. |
| 2014/0350720 A1 | 11/2014 | Lehmann et al. |
| 2014/0371904 A1 | 12/2014 | Parviainen |
| 2015/0012131 A1 | 1/2015 | Saltsov |
| 2015/0021349 A1 | 1/2015 | Sanders |
| 2015/0038898 A1 | 2/2015 | Palmer et al. |
| 2015/0048101 A1 | 2/2015 | Reddy et al. |
| 2015/0072300 A1 | 3/2015 | Wolpo |
| 2015/0072306 A1 | 3/2015 | Barnard |
| 2015/0079533 A1 | 3/2015 | Lowe |
| 2015/0174348 A1 | 6/2015 | Tunnell et al. |
| 2015/0174349 A1 | 6/2015 | Tunnell et al. |
| 2015/0191268 A1 | 7/2015 | Paz |
| 2015/0191294 A1 | 7/2015 | Paz |
| 2015/0221086 A1 | 8/2015 | Bertram |
| 2015/0232256 A1 | 8/2015 | Hoover et al. |
| 2015/0257980 A1 | 9/2015 | Fung et al. |
| 2015/0259110 A1 | 9/2015 | Blackburn |
| 2015/0266654 A1 | 9/2015 | Baarman et al. |
| 2015/0272825 A1 | 10/2015 | Lim et al. |
| 2015/0273165 A1 | 10/2015 | Hadash |
| 2015/0291344 A1 | 10/2015 | MacVittie et al. |
| 2015/0305671 A1 | 10/2015 | Yong-Kyu et al. |
| 2015/0317455 A1 | 11/2015 | Lehmann et al. |
| 2015/0320643 A1 | 11/2015 | Zhou |
| 2015/0328084 A1 | 11/2015 | Cash |
| 2015/0342830 A1 | 12/2015 | Bujalski et al. |
| 2015/0347713 A1 | 12/2015 | Seeger |
| 2015/0359667 A1 | 12/2015 | Brue |
| 2016/0012249 A1 | 1/2016 | Keppler |
| 2016/0016720 A2 | 1/2016 | Paz |
| 2016/0022542 A1 | 1/2016 | Lehmann et al. |
| 2016/0029962 A1 | 2/2016 | Hyde |
| 2016/0037916 A1 | 2/2016 | Hermann |
| 2016/0038377 A1 | 2/2016 | Tegborg et al. |
| 2016/0042150 A1 | 2/2016 | Moloughney |
| 2016/0066776 A1 | 3/2016 | Weiss et al. |
| 2016/0096014 A1 | 4/2016 | Ajiki |
| 2016/0107820 A1 | 4/2016 | MacVittie et al. |
| 2016/0113747 A1 | 4/2016 | Almutairi |
| 2016/0117480 A1 | 4/2016 | Ervin |
| 2016/0128906 A1 | 5/2016 | Baarman et al. |
| 2016/0132660 A1 | 5/2016 | Barajas et al. |
| 2016/0136056 A1 | 5/2016 | Lapham |
| 2016/0145031 A1 | 5/2016 | Reinhold et al. |
| 2016/0158107 A1 | 6/2016 | Dvorak et al. |
| 2016/0166766 A1 | 6/2016 | Schuster et al. |
| 2016/0180693 A1 | 6/2016 | Johnson |
| 2016/0203292 A1 | 7/2016 | Kamen et al. |
| 2016/0211693 A1 | 7/2016 | Stevens et al. |
| 2016/0213606 A1 | 7/2016 | Palmer et al. |
| 2016/0213843 A1 | 7/2016 | Despa et al. |
| 2016/0228333 A1 | 8/2016 | Bukstein et al. |
| 2016/0278899 A1 | 9/2016 | Heller |
| 2017/0027675 A1 | 2/2017 | Nahshon |
| 2017/0028178 A1 | 2/2017 | Skoda |
| 2017/0265978 A1 | 9/2017 | Borotto et al. |

(56) References Cited

U.S. PATENT DOCUMENTS

2017/0312181 A1   11/2017   Davis et al.
2017/0333649 A1   11/2017   Djupesland

FOREIGN PATENT DOCUMENTS

| WO | WO2004062717 A1 | 7/2004 |
| WO | WO2011151056 A1 | 12/2011 |
| WO | WO2015150240 A1 | 10/2015 |
| WO | WO2015172962 A1 | 11/2015 |
| WO | WO2015181693 A1 | 12/2015 |
| WO | WO2015196293 A1 | 12/2015 |
| WO | WO2015196336 A1 | 12/2015 |
| WO | WO2016064592 A1 | 4/2016 |
| WO | WO2016064688 A1 | 4/2016 |
| WO | WO2016064786 A1 | 4/2016 |
| WO | WO2016064906 A1 | 4/2016 |
| WO | WO2016064908 A1 | 4/2016 |
| WO | WO2016116591 A1 | 7/2016 |
| WO | WO2017064709 A1 | 4/2017 |
| WO | 2017218947 A1 | 12/2017 |

OTHER PUBLICATIONS

Written Opinion issued in PCT/US2019/022287 dated Jul. 16, 2019.
International Search Report issued in PCT/US2018/013440 dated Mar. 9, 2018.
Written Opinion issued in PCT/US2018/013440 dated Mar. 9, 2018.

* cited by examiner

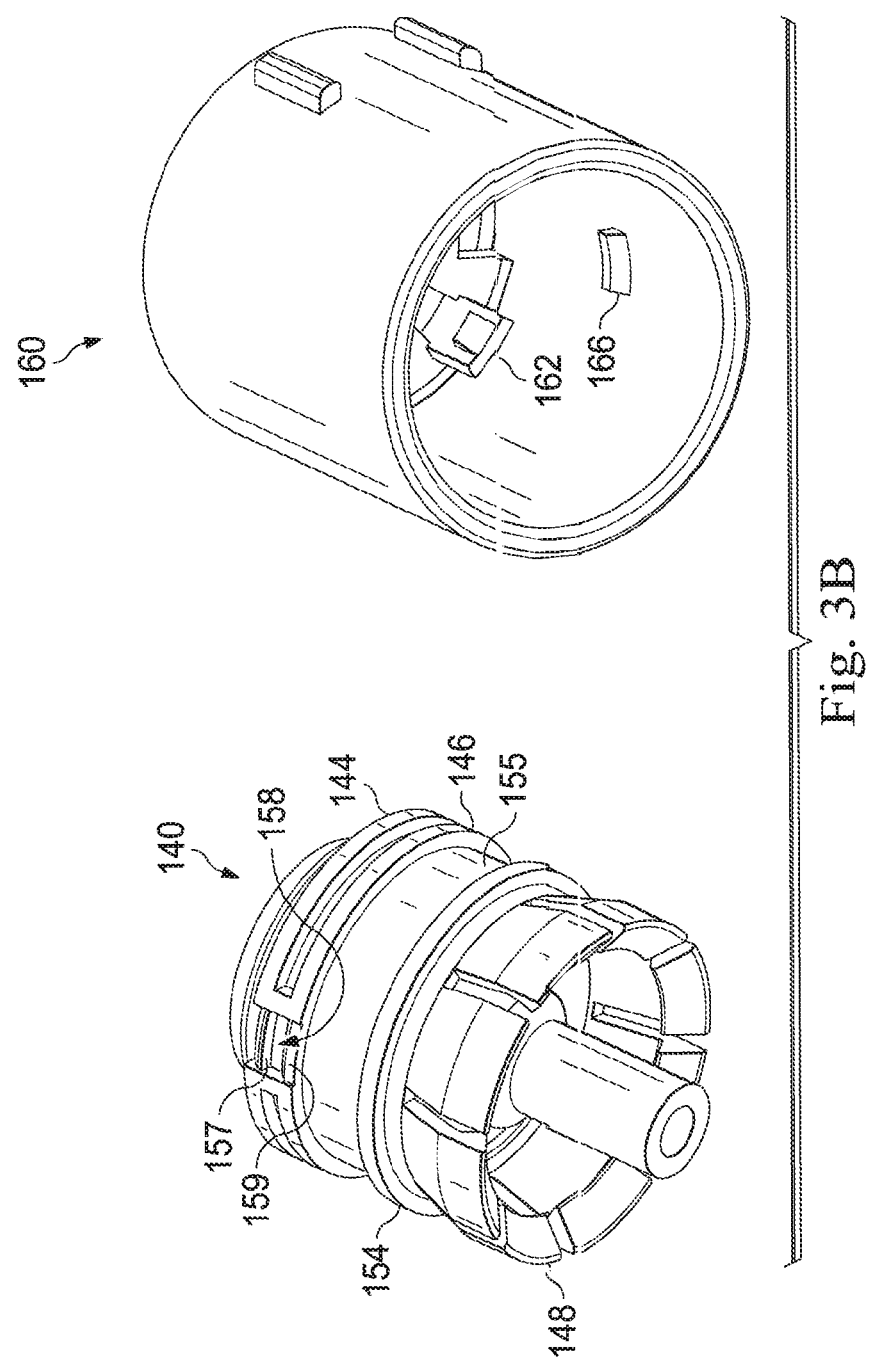

COMPUTERIZED ORAL PRESCRIPTION ADMINISTRATION FOR SECURELY DISPENSING A MEDICATION AND ASSOCIATED SYSTEMS AND METHODS

TECHNICAL FIELD

The present disclosure relates generally to pharmaceutical oral dose administration devices and computerized oral prescription administration (COPA) devices. For example, a locking cap may be implemented on a medication bottle to prevent unauthorized access to the medication and to facilitate secure dispensing of the medication to only the intended user.

INTRODUCTION

The history of pharmacology has produced a continual evolution of routes of administration, pharmaceutical formulations, dosage forms, and dosing devices in a continuing quest towards maximizing the effective benefit and relative costs of prescription medications. Administration of prescribed substances may begin in controlled healthcare settings, for example, at a healthcare facility or by a physician at a patient's home. Early-stage formulations may include liquid forms for parenteral (e.g., into a blood stream) and enteral (e.g., into a gastro-intestine) administration including elixirs, tonics, solutions, suspensions, syrups and eventually injections, intravenous (IVs), and epidurals. The early-stage formulations may be developed to produce advanced forms, for example, via mechanization and formulation research. The early-stage formulations, the advanced forms, and further research and clinical studies such as patient acceptances of the early-stage formulations and/or the advanced forms may contribute to the routes of administration, pharmaceutical formulations, dosage forms, and dosing devices.

As the healthcare treatment transitioned from limited emergency involvement into longer term chronic illness care, higher percentages of the prescribed medication administration shifted from the controlled healthcare settings to patient managed settings. In a patient managed setting, outside the control of a trained healthcare staff, the administration of liquid formulations may be difficult due to non-specific dosing instructions. Dosing based on teaspoon and/or tablespoon measurements may be vague and variable. Dosing cups may have different measurement formats, and thus may cause confusion in a patient managed setting. In addition, dosing cups are often separated from initial prescription bottles, and thus may lead to erroneous administration.

The advancements of mechanical manufacturing systems and pharmacology research enabled patient managed administrations of prescribed substances to shift from liquid formulations to pills (e.g., tablets or capsule-formulations), which may have increased shelf life and allow for patient ease of use, dosing exactness, and production cost reductions. Thus, a majority of oral medications in patient managed settings are now pills. Additionally, there is an increased interest in microparticulate formulations including pellets, granules, micro particles, mini tablets, and the like. However, patients, such as infants, elderly, or impaired patients, that cannot or prefer not to swallow tablets or capsule-formulations may be given enteral oral liquid prescriptions through dosing syringes in patient managed settings. In addition, parenteral liquid formulations are still commonly administered in controlled healthcare settings since the parenteral liquid formulations often have the fastest rate of absorption and the most expedient success in the desired result and can improve localized administration, inventory control, fraud prevention, and administration path audit capability.

Depending on the entity managing the administration of a drug, various forms of the drug may be developed to meet expectations, needs, and challenges of different entities. While there are some exceptions based on effectiveness and toxicity, most pharmaceutical manufacturers may produce multiple formulations of drugs to support different routes of administration and dosing.

There is a growing demand for drug administration in patient controlled or managed settings as consumers increasingly engage in preventative or resultative treatment plans, which involve drug administration in patient controlled settings. For example, outpatient surgeries and/or one-day inpatient surgery stays are increasingly common for significant medical procedures, which may involve subsequent drug administrations at a patient's home. In addition, as the population ages, the demand for prescription management increases. Consumers may take multiple over-the-counter and/or prescribed medicines daily, where the medicines are commonly in the form of pills. Unfortunately, the ease-of-use of pills and the increasing number of consumers engaged in chronic patient managed treatment plans has led to misuse and mismanagement of many drug classes.

For example, pill forms are lightweight, portable, recipient non-specific, difficult for inventory management, don't carry individual identification numbers, have extensive shelf life, and are inexpensive to produce. Thus, the intakes or usages of pills are difficult to control once outside of healthcare managed environments. In addition, to achieve the economy of scale in the manufacturing process, pill production is scheduled based on maximizing the output of the machines, materials, and/or ingredients available instead of based on future demands. With a few exceptions, a minimal amount of the pills produced are wasted since pills remain active for a long time. Pills proliferate our society and have become conduits to addiction and abuse.

One such patient managed treatment that is highly susceptible to prescription misuse and mismanagement is opioid pain treatment. For example, according to the Food and Drug Administration (FDA), approximately 100 million people in the United States (US) suffer from pain in a given year. About 9 to 12 million of the pain sufferers have chronic or persistent pain, while the remaining pain sufferers have short-term pain from injuries, illnesses, or medical procedures. In 2014, the Centers for Disease Control and Prevention reported that the number of annual opioid prescriptions in the US is about equal to the number of adults in the US population. While pain sufferers should benefit from skillful and appropriate pain management, the misuse or addiction of opioids needs to be controlled. FDA leaders and physicians attempt to address the opioid epidemic by balancing two complementary principles: deal aggressively with opioid misuse and addiction while protecting the well-being of people experiencing acute or chronic pains. However, the pain sufferers in areas where reforms, policies, and restrictions aimed at opioid misuse have been implemented may not experience the balance. Some states have implemented additional known addict or misuser databases that must be checked by providers prior to prescribing. However, physicians may not check the databases prior to prescribing due to the burden of using the systems and/or they may not want to restrict access by true chronic pain sufferers. Other states have implemented reporting and audit trails to track physicians that have prescribed from the opioid family. However, to avoid the additional steps and potentials for audit scrutiny, some physicians may refuse to offer pain management or short-term pain prescriptions, and may refer all cases to pain clinics.

Attempts at improved patient education, enhanced labeling, and restrictive prescribing have led to higher costs for providers, patients, pharmacies, and insurance companies and less overall effectiveness for the patients. In the end, true pain sufferers struggle to have access to opioids while opioid misusers continue to manipulate the available avenues for access regardless of the apparent oversights put in place. Policies and plans at various levels have not been successful and are not sufficient to control or reduce the misuse of prescription drugs. Accordingly, improved devices, systems, and methods for drug administration are needed.

SUMMARY

The following summarizes some aspects of the present disclosure to provide a basic understanding of the discussed technology. This summary is not an extensive overview of all contemplated features of the disclosure, and is intended neither to identify key or critical elements of all aspects of the disclosure nor to delineate the scope of any or all aspects of the disclosure. Its sole purpose is to present some concepts of one or more aspects of the disclosure in summary form as a prelude to the more detailed description that is presented later.

The present disclosure relates generally to pharmaceutical oral dose administration devices and computerized oral prescription administration (COPA) devices. These COPA devices, systems, and methods facilitate the secure dispensing of medication to an intended user. In this regard, the COPA device can be coupled to a housing, which may include a medication housing (e.g., bottle, tube, casing, etc.). The medication housing may include a threaded opening to which a locking cap of the present disclosure is secured. To prevent unauthorized access to the substance (e.g., medication, a prescribed substance, etc.) within the medication housing, the medication housing may be coupled to the locking cap. The locking cap may include a member that is registered to the intended user via a unique identifier. The locking cap can determine whether the intended user is attempting to access the medication within the medication housing. In some instances, the medication may only be dispensed when the unique identifier associated with the intended user is verified. Additional verification devices, systems, and methods may also be used to authenticate the intended user. For example, one or more biometric sensors may be used to detect biometric attribute(s) of the intended user to authenticate the intended user.

In one embodiment, a member for securely dispensing a substance to an intended user is provided. The member includes a first member configured to threadedly engage with a housing containing the substance; a second member coupled to the first member, the second member configured to fixedly secure the first member to the housing; a third member including a cavity sized and shaped to selectively receive the second member; and a valve coupled to the first member such that: when the second member is received within the cavity of the third member, the valve is in an open state that allows the substance to be dispensed from the housing to the intended user in response to a processor determining that a unique biometric attribute of the intended user is detected, and when the second member is not received within the cavity of the third member, the valve is in a closed state that prevents the substance from being dispensed from the housing.

In some embodiments, the member further comprises a biasing member configured to bias the valve to the closed state when the second member is not received within the cavity of the third member. In some embodiments, when the second member is received within the cavity of the third member, the biasing member is compressed. In some embodiments, the first member comprises a plurality of latching members configured to encase a lip of the housing, the plurality of latching members configured to prevent removal of the first member from the housing in an axial direction. In some embodiments, the second member includes a distal portion configured to encase the plurality of latching members to prevent removal of the plurality of latching members from the lip of the housing in a radial direction. In some embodiments, the plurality of latching members are circumferentially arranged around a circumference of the first member. In some embodiments, the first member comprises at least one proximal latching member. In some embodiments, the second member comprises at least one latch configured to engage with the at least one proximal latching member of the first member to prevent removal of the second member from the first member in an axial direction. In some embodiments, the valve includes a longitudinal axis, and the second member is configured to rotate about the longitudinal axis of the valve when the second member is coupled to the first member.

In some embodiments, the unique biometric attribute comprises a unique dentition of the intended user. In some embodiments, the member further comprises a mouthpiece having a sensor array, wherein the substance is dispensed from the housing to a mouth of the intended user through the mouthpiece. In some embodiments, the processor is configured to determine that the unique biometric attribute of the intended user is detected by the sensor array. In some embodiments, the second member comprises one or more sensors positioned on an upper surface of the second member, the one or more sensors configured to provide a unique identifier associated with the intended user. In some embodiments, the third member comprises one or more detectors positioned on a lower surface of the third member, the one or more detectors configured to be in contact with the one or more sensors of the second member when the second member is received within the cavity of the third member. In some embodiments, the one or more detectors of the third member are configured to communicate with the one or more sensors of the second member to receive the unique identifier associated with the intended user. In some embodiments, the processor is further configured to cause the substance to be dispensed from the housing to a mouth of the intended user in response to determining that the one or more detectors received the unique identifier associated with the intended user.

In one embodiment, a method of securely dispensing a substance to an intended user is provided. The method includes moving a valve of a locking cap fixedly secured to a housing containing the substance to an open state that allows the substance to be dispensed from the housing to the intended user; determining that a unique biometric attribute of the intended user is detected; and dispensing the substance from the housing to the intended user in response to determining that the unique biometric attribute of the intended user is detected.

In some embodiments, the method further comprises fixedly securing the locking cap to the housing. In some embodiments, fixedly securing the locking cap to the housing comprises encasing a lip of the housing with a plurality of latching members of a first member of the locking cap, wherein the first member is threadedly engaged to the housing. In some embodiments, fixedly securing the locking cap to the housing further comprises coupling a second member of the locking cap with the first member of the locking cap. In some embodiments, coupling the second member of the locking cap to the first member of the locking cap comprises encasing the plurality of latching members of the first member with a distal portion of the second member. In some embodiments, moving the valve of the locking cap to the open state comprises inserting a second member of the locking cap into a cavity of a third member of the locking cap. In some embodiments, determining that the unique biometric attribute of the intended user is detected comprises determining that a unique dentition of the intended user is positioned within a recess of a mouthpiece. In some embodiments, determining that the unique dentition of the intended user is positioned within the recess of the mouthpiece includes determining, by a processor, that the unique dentition of the intended user is positioned within the recess of the mouthpiece.

In some embodiments, the method further comprises receiving, by one or more detectors of the locking cap, a unique identifier associated with the intended user from one or more sensors of the locking cap. In some embodiments, the dispensing the substance from the housing to the intended user further comprises dispensing the substance in response to determining that the one or more detectors received the unique identifier associated with the intended user.

In one embodiment, a system for securely dispensing a substance to an intended user is provided. The system includes a device housing and a locking cap coupled to the device housing. The locking cap includes a first member configured to threadedly engage with a housing containing the substance; a second member coupled to the first member, the second member configured to fixedly secure the first member to the housing; a third member including a cavity sized and shaped to selectively receive the second member; and a valve coupled to the first member such that: when the second member is received within the cavity of the third member, the valve is in an open state that allows the substance to be dispensed from the housing; and when the second member is not received within the cavity of the third member, the valve is in a closed state that prevents the substance from being dispensed from the housing. The system further includes a mouthpiece coupled to the device housing, the mouthpiece including a recess; and a processor configured to: determine that a unique dentition of the intended user is positioned within the recess of the mouthpiece; and cause the substance to be dispensed from the housing to a mouth of the intended user in response to determining that the unique dentition of the intended user is positioned within the recess of the mouthpiece.

In some embodiments, the mouthpiece includes a capacitive sensor array configured to obtain data regarding dentition positioned within the recess of the mouthpiece. In some embodiments, the data obtained by the capacitive sensor array includes a capacitive map associated with the intended user. In some embodiments, the processor is further configured to compare a capacitive map associated with a user of the mouthpiece to a predetermined capacitive map associated with the intended user.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 3B is a perspective view of a first member and a second member of a locking cap according to embodiments of the present disclosure.

DETAILED DESCRIPTION

Figure 1:
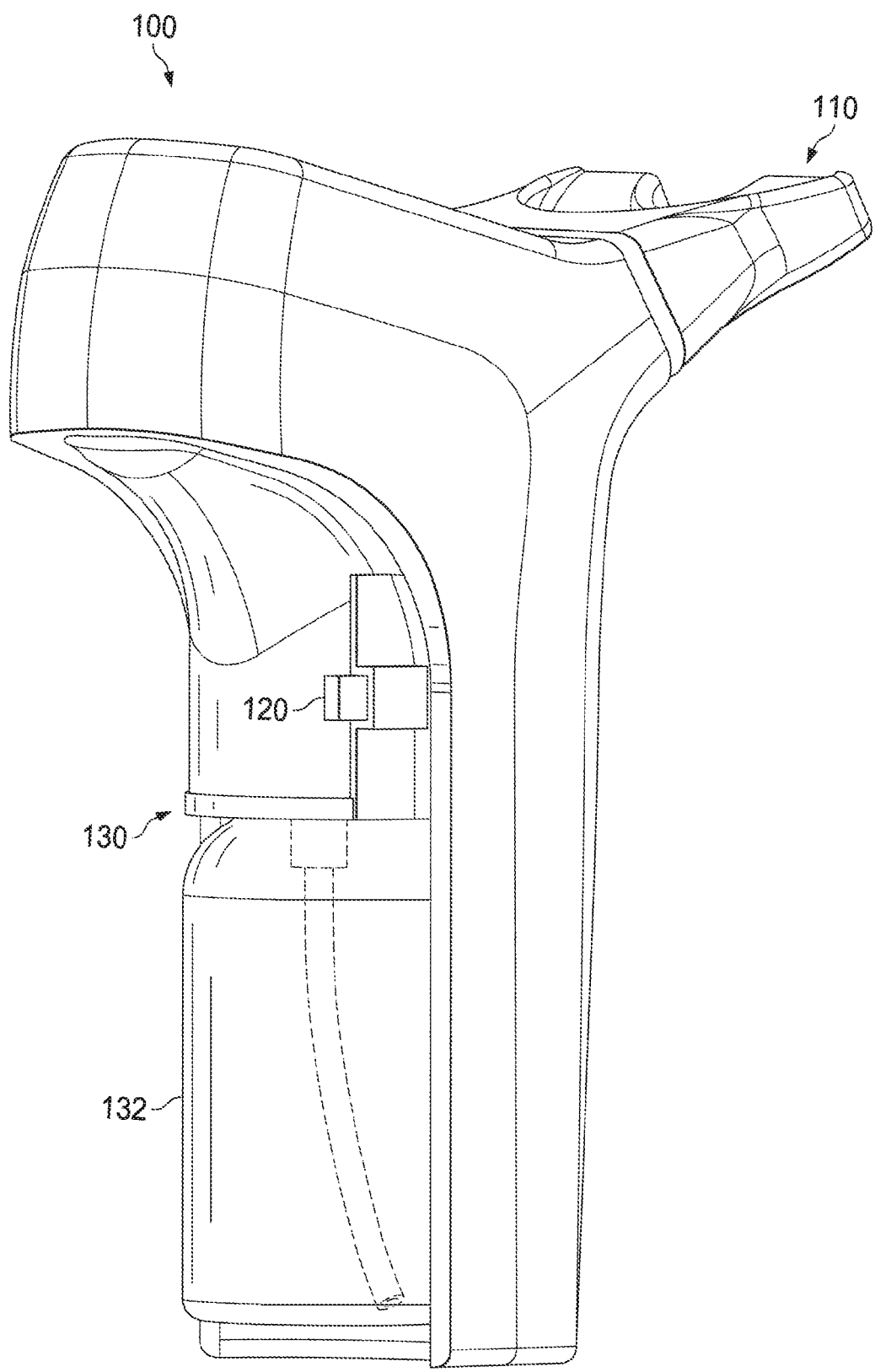
FIG. 1 is a perspective view of a medication housing coupled to a device housing according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates.

Embodiments of the present disclosure provide mechanisms for securely dispensing a substance to an intended user. In an embodiment, a locking cap includes a first member threadedly engageable with a housing (e.g., a medication bottle) containing a substance. The substance may be a prescription medication or an over-the-counter medication. The locking cap may include a second member coupled to the first member. The second member may fixedly secure the first member to the housing. The locking cap may include a third member including a cavity sized to receive the second member. The second member may be selectively received within the cavity such that the second member may be removed from the cavity after being inserted within the cavity. The locking cap may include a valve coupled to the first member. The valve may be movable between an open state and a closed state. When the second member is received within the cavity of the third member, the valve may be in the open state. The open state allows the substance to be dispensed from the housing to the intended user. The substance may be dispensed to the intended user in response to a processor determining that a unique biometric attribute of the intended user is detected. When the second member is not received within the cavity of the third member, the valve is in the closed state. The closed state prevents the substance from being dispensed from the housing. The processor may be configured to determine when the second member is received within the cavity of the third member. In an embodiment, the second member may be registered to the intended user.

The disclosed embodiments may provide several benefits. For example, the employment of the locking cap can ensure that the prescribed medications within the housing are delivered only to the intended recipient and are not tampered with. Thus, the disclosed embodiments may avoid misuse (intentional and accidental) as well as mismanagement of prescription medications. The disclosed embodiments may deliver a precise dosage of prescribed medications to patients. This may especially benefit patients that are elderly, impaired, or have behavioral issues that may limit their abilities to self-administer prescribed medications. In addition, the employment of the locking cap can facilitate one device housing, which may include the locking cap and the attached medication housing, being used for several users (with only one intended user registered to the locking cap at a time). Thus, the disclosed embodiments may avoid burdensome production costs.

FIG. 1 is a perspective view of a medication housing 132 coupled to a device housing 100 according to embodiments of the present disclosure. In several embodiments, the device housing 100 is coupled to a COPA device 110. The device housing 100 includes a release button 120. The medication housing 132 may be coupled to the device housing 100 via a locking cap 130. The device housing 100 may be sized and shaped for handheld use. For example, the device housing 100 may be structurally arranged to be gripped by a single hand of a user by placing the user's fingers and palm around the device housing 100. The device housing 100 may be any suitable shape, such as a cylinder, a rectangular prism, a cube, portions thereof, and/or any combination thereof. In some embodiments, the device housing 100 includes a removable back cover that covers the medication housing 132. In such embodiments, the back cover may also cover the release button 120 such that the release button 120 is only accessible when the back cover is removed from the device housing 100. In some examples, the back cover may be clear so that a medication label of the medication housing 132 may be visible when the back cover is coupled to the device housing 100.

The back cover may be removed to allow an authorized person, such as a pharmacist, to access the medication housing 132 and refill and/or replace the medication housing 132 as needed. In some embodiments, to remove the back cover, the authorized person may unlock the back cover from the device housing 100. Then, the authorized person may remove an empty medication housing 132 from the device housing 100 by pressing the release button 120. In some embodiments, the authorized person may refill the medication housing 132 with a prescribed substance and place the medication housing 132 back into the device housing 100. After placing the medication housing 132 within the device housing 100, the authorized person may lock the back cover onto the device housing 100.

In some embodiments, the COPA device 110, which may include a mouthpiece, may have one or more sensors or sensor arrays used to detect a unique dentition of an intended user. In some examples, the sensors of the mouthpiece may include a capacitive sensor array. The capacitive sensor array may be configured to detect a capacitive map associated with a detected input from a current user of the COPA device 110. The capacitive map may be associated with a dentition of the current user of the COPA device 110. In some examples, the capacitive map is associated with a unique dentition of the intended user. A processor may determine whether the intended user's unique dentition is positioned within a recess of the COPA device 110. For example, the processor may compare the capacitive map associated with the detected input from the current user of the COPA device 110 to a predetermined capacitive map associated with the intended user's unique dentition. From this comparison, the processor determines whether there is a match between the current user of the COPA device 110 and the intended user of the COPA device 110. If there is a match, the processor may cause the substance to be dispensed from the medication housing 132 to the intended user. In some embodiments, the processor is included in the device housing 100. In alternative embodiments, the processor is included in the COPA device 110. In further alternative embodiments, the processor is included in a system separate from the device housing 100 and the COPA device 110.

Additional details regarding the device housing 100 and the COPA device 110 may be found in U.S. patent application Ser. No. 15/406,043, now U.S. Pat. No. 9,731,103, filed Jan. 13, 2017, U.S. patent application Ser. No. 15/674,046, now U.S. Pat. No. 10,188,840, filed Aug. 10, 2017, U.S. patent application Ser. No. 15/708,045, now U.S. Pat. No. 9,981,116, filed Sep. 18, 2017, U.S. patent application Ser. No. 15/958,809, filed Apr. 29, 2018, U.S. patent application Ser. No. 16/001,498, filed Jun. 6, 2018, and U.S. patent application Ser. No. 16/246,122, filed Jan. 11, 2019, each of which are hereby incorporated by reference in their entireties.

Figure 2:
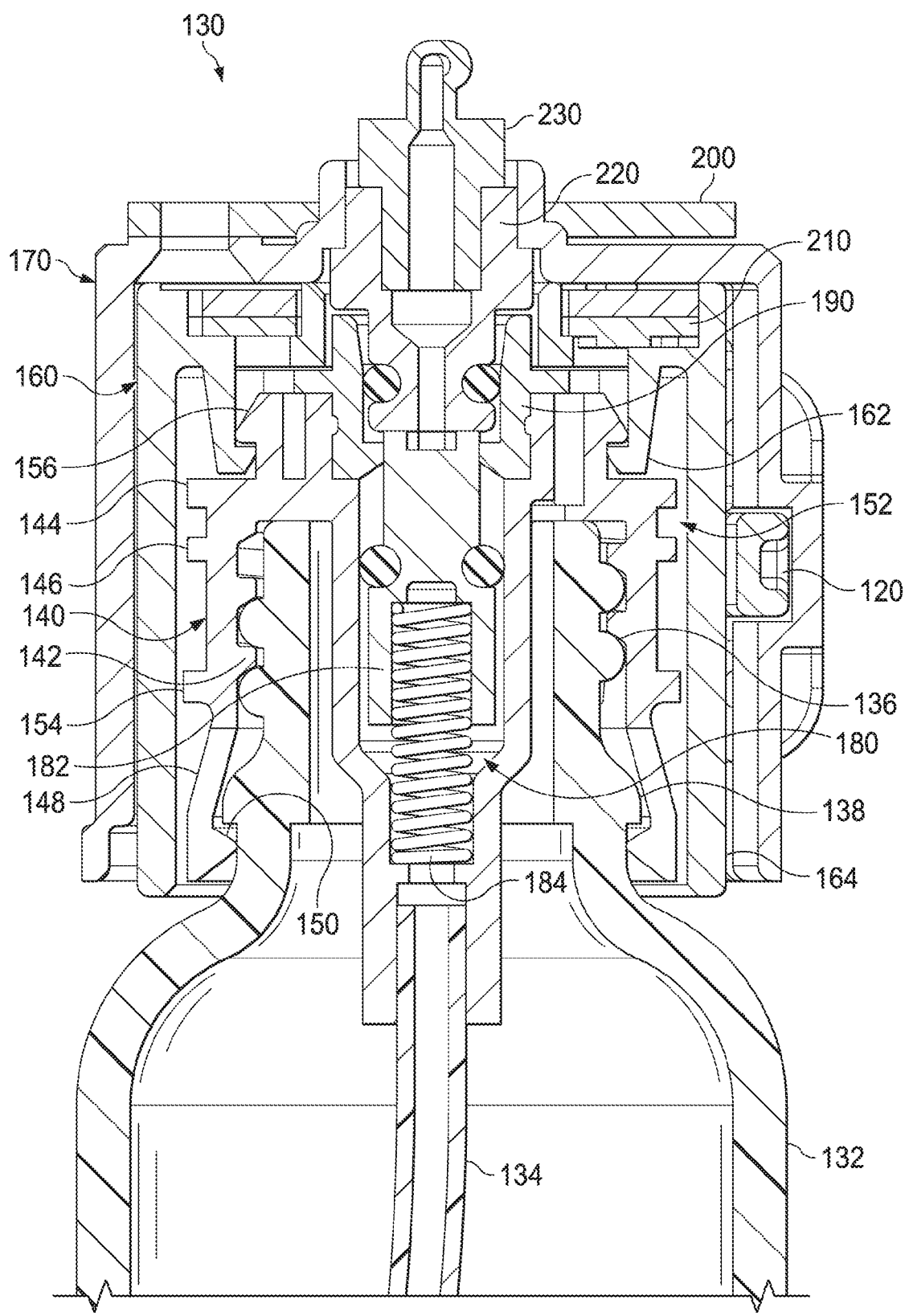
FIG. 2 is a cross-sectional view of a locking cap coupled to a housing according to embodiments of the present disclosure.

FIG. 2 is a cross-sectional view of the locking cap 130 coupled to the medication housing 132 according to embodiments of the present disclosure. The medication housing 132 includes threads 136 and a lip 138. The locking cap 130 includes a first member 140, a second member 160, and a third member 170. The first member 140 includes grooves 142 corresponding to the threads 136 of the housing 132. The grooves 142 receive the threads 136. In this manner, the first member 140 and the housing 132 can be threadedly coupled. The first member 140 further includes an upper rim 144, a lower rim 146, at least one latching member 148, a lower tab 150 corresponding to each latching member 148, a recess 152 defined by the upper and lower rims 144, 146, a ledge 154, and at least one upper tab 156, which may also be referred to as a proximal latching member. In some embodiments, the second member 160 includes at least one upper tab 162 corresponding to the upper tab 156 of the first member 140. The second member 160 further includes a distal portion 164 and a circuit board 210. In some embodiments, the circuit board 210 may be coupled to one or more sensors or sensor arrays. In alternative embodiments, the sensor(s) may be integrated within the circuit board 210.

In some embodiments, the third member 170 includes the release button 120. In alternative embodiments, the third member 170 may be included as part of the device housing 100. The third member 170 further includes a circuit board 200 positioned on a top surface, which may be an upper surface, of the third member 170. In some embodiments, the circuit board 200 may be coupled to one or more detectors or detector arrays. In alternative embodiments, the detector(s) may be integrated within the circuit board 200. In some examples, the detectors are in communication with the sensors of the second member 160. A processor may use the data obtained by the sensors to determine whether the second member 160 is coupled to the third member 170. In some embodiments, the second member 160 is coupled to the third member 170 when the second member 160 is received within a cavity of the third member 170, which will be discussed in further detail below.

In some embodiments, the locking cap 130 includes a valve assembly 180. The valve assembly 180 includes a valve 182, a biasing member 184, and a fluid connector 190. In some embodiments, the valve assembly 180 includes a check valve. It is to be understood that the valve assembly 180 may include any other suitable type of valve, such as a ball valve, a diaphragm valve, a globe valve, a needle valve, a gravity valve, a duck-billed valve, etc. In some embodiments, the biasing member 184 is a spring. In other embodiments, the biasing member 184 may be any other suitable type of component configured to bias the valve 182 in a particular direction. In some examples, the biasing member 184 biases the valve 182 to the closed state when the second member 160 is not received within the cavity 172 of the third member 170. The valve assembly 180 may be integrally formed as part of the first member 140. In other embodiments, the valve assembly 180 may be a separate component received within and coupled to the first member 140. As shown in the embodiment of FIG. 2, the valve assembly 180 is received within the first member 140 and is connected to a dip tube 134. The dip tube 134 is positioned within the housing 132 and is used to transport a substance, which may be a prescribed substance, from the housing 132 to the intended user.

In some embodiments, the third member 170 includes a coupling member 220 to couple the valve assembly 180 to the device housing 100. As shown in the embodiment of FIG. 2, the fluid connector 190 of the valve assembly 180 is coupled to the coupling member 220. As also shown in the embodiment of FIG. 2, the coupling member 220 is coupled to a pump 230. In some embodiments, the pump 230 is included as part of the device housing 100. Therefore, in some embodiments, the coupling member 220 facilitates the connection between the locking cap 130 and the device housing 100 via the pump 230. This connection allows for the prescribed substance to be dispensed from the housing 132, through the valve assembly 180, through the pump 230, and to the intended user. In some examples, the prescribed substance is also dispensed through the COPA device 110 before reaching the intended user. In such examples, the prescribed substance is dispensed into a mouth of the intended user.

Figure 3A:
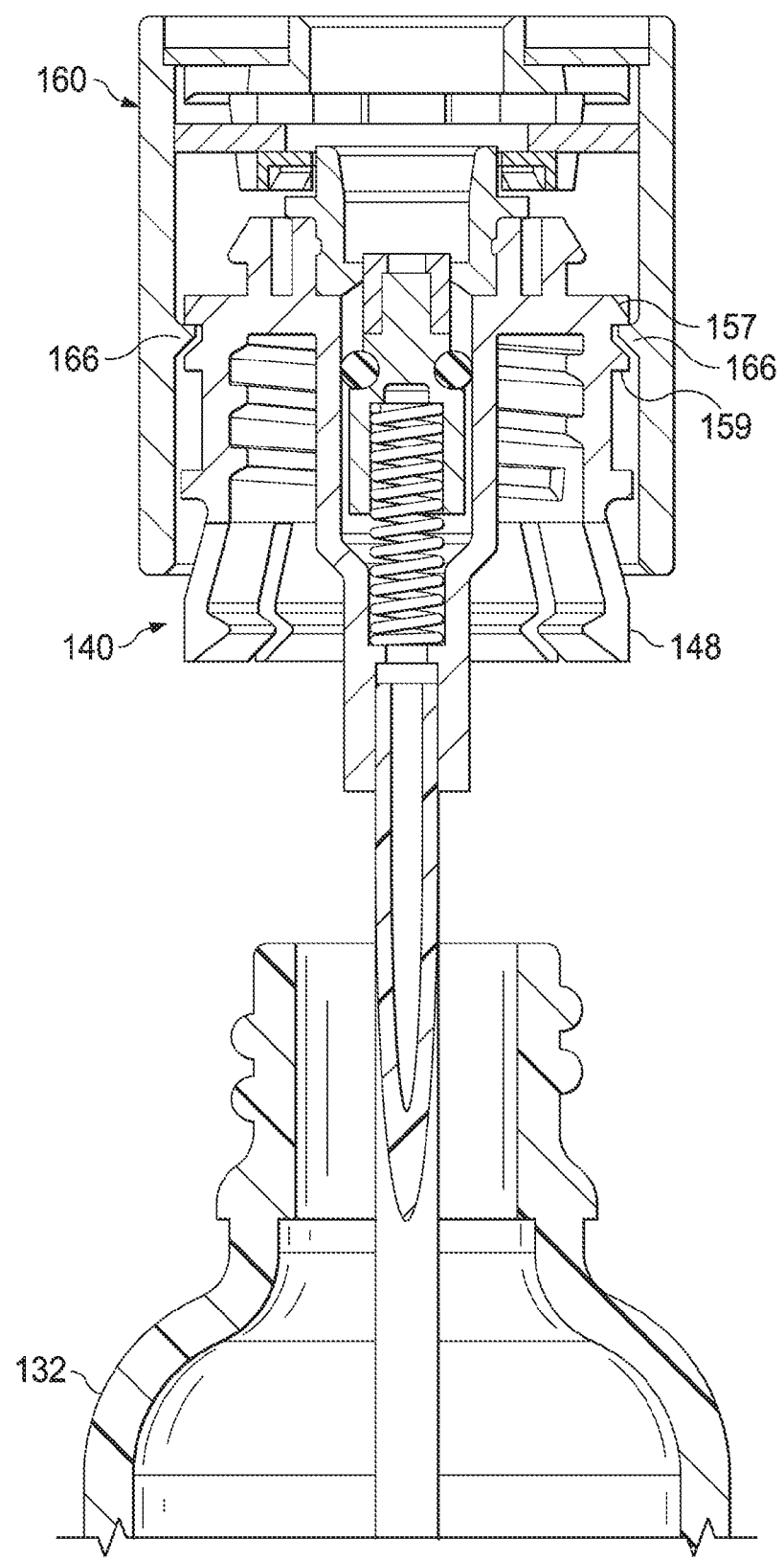
FIG. 3A is a cross-sectional view of a first member and a second member of a locking cap spaced from a housing according to embodiments of the present disclosure.

FIG. 3A is a cross-sectional view of the first member 140 and the second member 160 spaced from the housing 132 according to embodiments of the present disclosure. FIG. 3B is a perspective view of the first member 140 and the second member 160 according to embodiments of the present disclosure. As shown in the embodiment of FIG. 3B, the latching members 148 are circumferentially arranged around a circumference of the first member 140. Each latching member 148 may be separated by a gap to provide greater flexibility and ease of movement for each latching member 148. For example, each latching member 148 may move and flex independently of the other latching members 148 when the first member 140 is coupled to the housing 132. In some embodiments, the first member 140 includes eight latching members 148, as shown in FIG. 3B. However, it is to be understood that the first member 140 may include any other desired number of latching members, which may be less than eight or more than eight latching members. In alternative examples, the first member 140 may include one continuous latching member 148, excluding any gaps, that extends around the circumference of the first member 140.

In some embodiments, the ledge 154 of the first member 140 is positioned in close proximity to the latching members 148. For example, the ledge 154 may be positioned at a connection point where the latching members 148 connect with a main body 155 of the first member 140. As shown in the embodiment of FIG. 3B, the upper rim 144 and the lower rim 146 are spaced from the ledge 154. In alternative embodiments, the ledge 154 may be spaced from the latching members 148, and the ledge 154 may be in close proximity to the lower rim 146. In some embodiments, the first member 140 further includes an upper lip 157 and a lower lip 159. The upper and lower lips 157, 159 are spaced from each other such that a locking groove 158 is defined between the upper and lower lips 157, 159. In some embodiments, the upper lip 157 is aligned with the upper rim 144, and the lower lip 159 is aligned with the lower rim 146. The upper and lower rims 144, 146 may together form a locking ring. The locking ring may include one or more locking grooves 158. In some examples, as shown in the embodiment of FIG. 3A, the first member 140 includes two locking grooves 158. In several examples, the second member 160 includes a locking tab 166 that is sized and shaped to fit within the locking groove 158. The second member 160 may include as many locking tabs 166 as there are locking grooves 158 such that each locking groove 158 receives a corresponding locking tab 166. In some examples, the locking ring may include as many locking grooves 158 as needed and/or desired (e.g., one, two, three, four, etc.).

In some embodiments, the second member 160 is coupled to the first member 140 by first pushing the second member 160 onto the first member 140 such that each locking tab 166 of the second member 160 travels over a corresponding upper lip 157 and is received by a corresponding locking groove 158 of the first member 140. When the locking tabs 166 are positioned within the locking grooves 158, the second member 160 is in a first position relative to the first member 140. In some embodiments, when the second member 160 is in the first position relative to the first member 140, the second member 160 and the first member 140 are rotationally locked relative to each other. Thus, when the second member 160 is rotated, the first member 140 rotates with the second member 160. Therefore, to attach the first member 140 to the housing 132, the first member 140 is placed on top of the housing 132. The second member 160 may then be rotated (e.g., in a clockwise direction or in a counter-clockwise direction) to screw the first member 140 onto the housing 132. In alternative embodiments, the first member 140 may be screwed onto the housing 132 without being connected to the second member 160. In such embodiments, the second member 160 may be coupled to the first member 140 after the first member 140 is coupled to the housing 132.

Figure 4A:
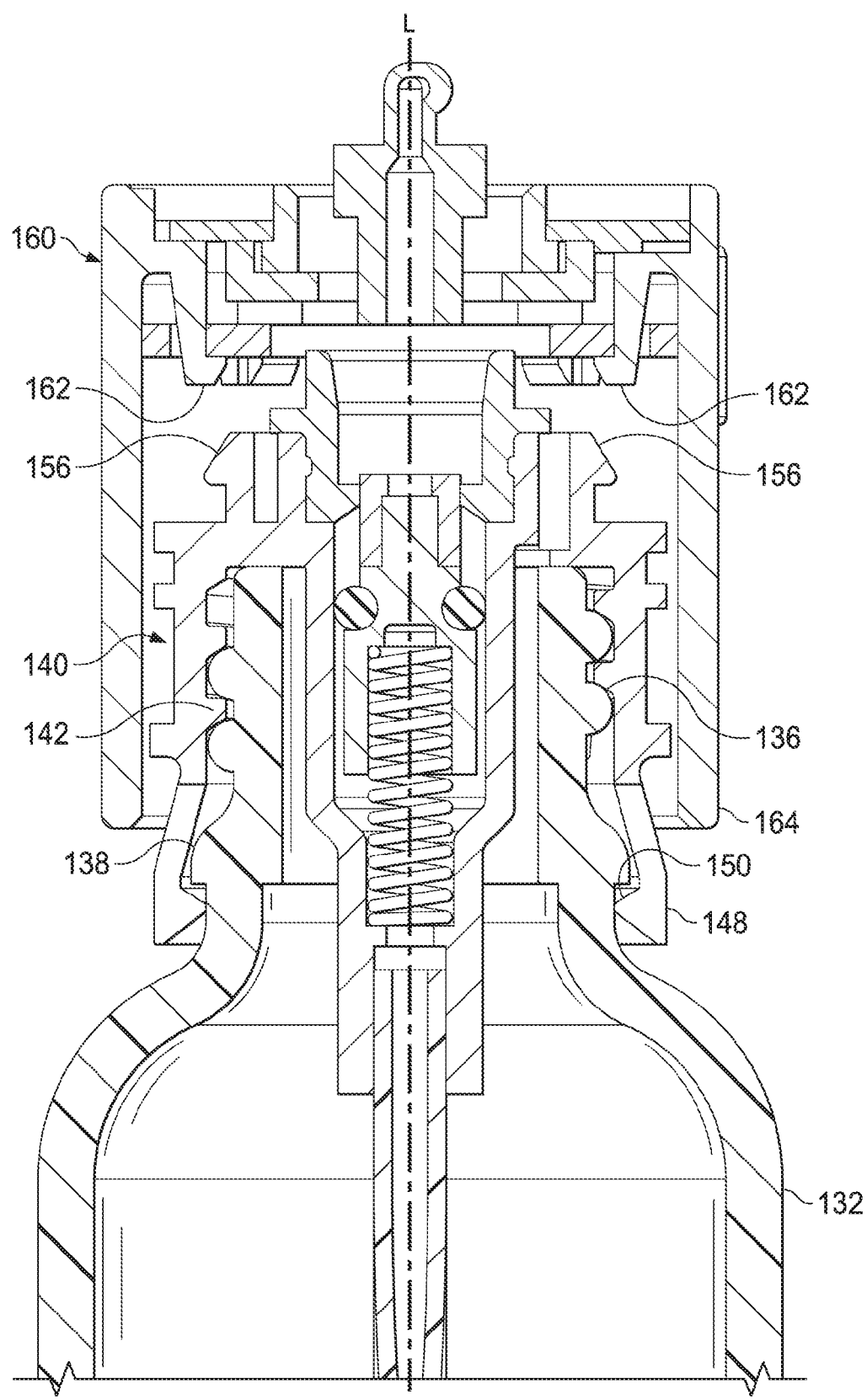
FIG. 4A is a cross-sectional view of a first member of a locking cap coupled to a housing and a second member of the locking cap coupled to the first member according to embodiments of the present disclosure.

FIG. 4A is a cross-sectional view of the first member 140 coupled to the housing 132 and the second member 160 coupled to the first member 140 according to embodiments of the present disclosure. In some embodiments, the second member 160 is rotated until the lower tab 150 of each of the latching members 148 of the first member 140 travels over and then engages with the lip 138 of the housing 132. In such embodiments, the lower tabs 150 may engage with the lip 138 by resting beneath the lip 138 and/or contacting a bottom portion of the lip 138. In this position, the first member 140 is fixedly secured to the housing 132 in a longitudinal direction, such as a direction substantially parallel to a longitudinal axis L of the biasing member 184 of the valve assembly 180. The longitudinal direction may also be referred to as an axial direction. After the first member 140 is fixedly secured to the housing 132, the second member 160 may be moved to a second position where the second member 160 is fixedly secured to the first member 140.

Figure 4B:
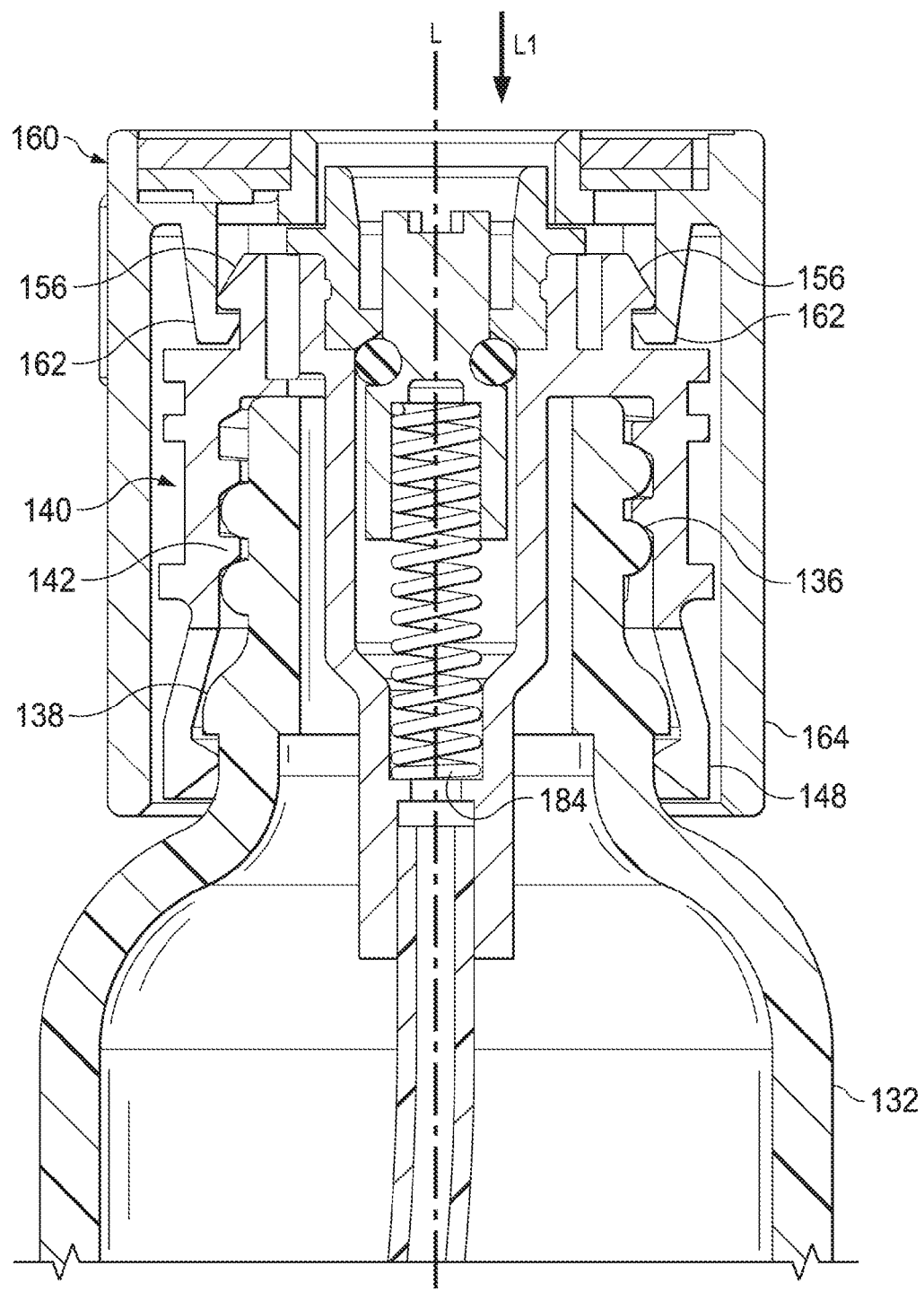
FIG. 4B is a cross-sectional view of a first member of a locking cap coupled to a housing and a second member of the locking cap coupled to the first member according to embodiments of the present disclosure.

FIG. 4B is a cross-sectional view of the first member 140 coupled to the housing 132 and the second member 160 coupled to the first member 140 according to embodiments of the present disclosure. In the embodiment shown in FIG. 4B, the second member 160 is in the second position relative to the first member 140. As shown, the upper tab 162 has traveled past and engaged with the upper tab 156 of the first member. Accordingly, the second member 160 is fixedly secured to the first member 140 in the longitudinal direction, which may also be referred to as an axial direction and is substantially parallel to the longitudinal axis L. As further shown in the embodiment of FIG. 4B, the distal portion 164 of the second member 160 encases the latching members 148 of the first member 140. Accordingly, the first member 140 is fixedly secured to the housing 132 in a radial direction, which may be a direction substantially perpendicular to the longitudinal axis L. Therefore, in some examples, when the second member 160 is in the second position relative to the first member 140, the first member 140 is fixedly secured to the housing 132 in both the longitudinal and radial directions. In such examples, the first member 140 and the second member 160 may be irreversibly fixedly engaged with the housing 132. Thus, the only way to remove either the first member 140 or the second member 160 from the housing 132 is to break one or more pieces of the locking cap 130. The first member 140 and the second member 160 may be irreversibly fixedly engaged with the housing 132 in one or both of the longitudinal and radial directions.

Figure 4C:
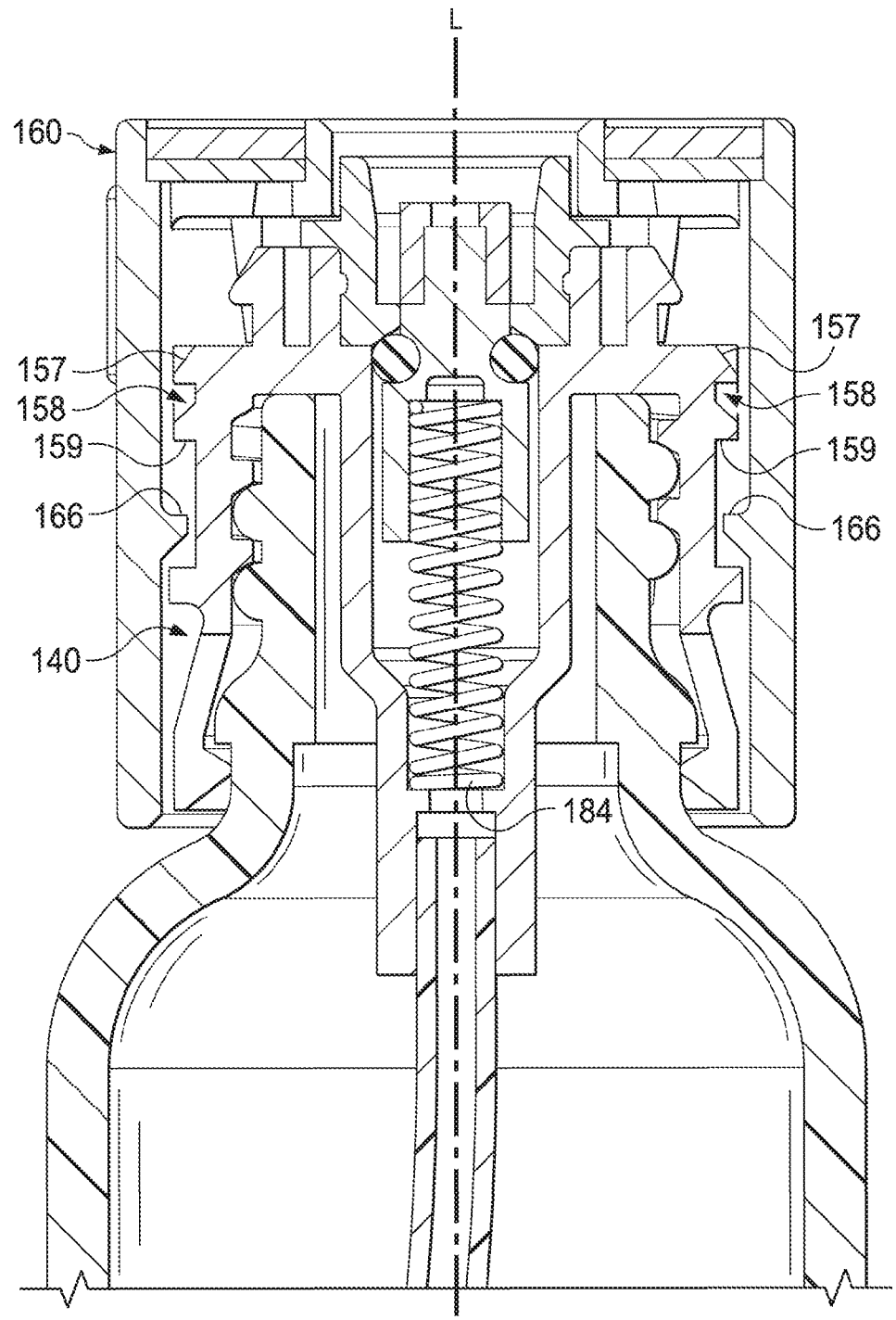
FIG. 4C is a cross-sectional view of a first member of a locking cap coupled to a housing and a second member of the locking cap coupled to the first member according to embodiments of the present disclosure.

FIG. 4C is a cross-sectional view of the first member 140 coupled to the housing 132 and the second member 160 according to embodiments of the present disclosure. In some embodiments, when the second member 160 is in the second position relative to the first member 140, the locking tabs 166 of the second member 160 are between the lower lip 159 and the ledge 154. Thus, to move from the first position to the second position, the second member 160 is pushed in a direction L1, which is substantially parallel to the longitudinal axis L. When the second member 160 moves from the first position to the second position, the locking tabs 166 move from being within the locking grooves 158 to being between the lower lip 159 and the ledge 154. During this transition from the first position to the second position, the locking tabs 166 travel over and past the lower lip 159.

In several examples, the distal portion 164 of the second member 160 is made of a harder and/or more rigid material than the latching members 148 of the first member 140. Therefore, the distal portion 164 restrains and/or contains any attempted radial movement of the latching members 148. Radial movement may occur if a user tries to remove the first member 140 from the housing 132. In some embodiments, when the second member 160 is in the second position with respect to the first member 140, the second member 160 and the first member 140 are no longer rotationally locked with respect to each other. Thus, in such embodiments, the second member 160 is freely rotatable around the first member 140. When the housing 132 is coupled to the device housing 100, the authorized person, for example, may rotate the housing 132 to a position where an information label of the housing 132 is facing the back cover of the device housing 100. In this position, a user is able to read the information label while the housing 132 is locked within the device housing 100. The information label may include information about the prescribed substance, such as type of substance, amount of substance, dosage instructions for the substance, etc.

Figure 5A:
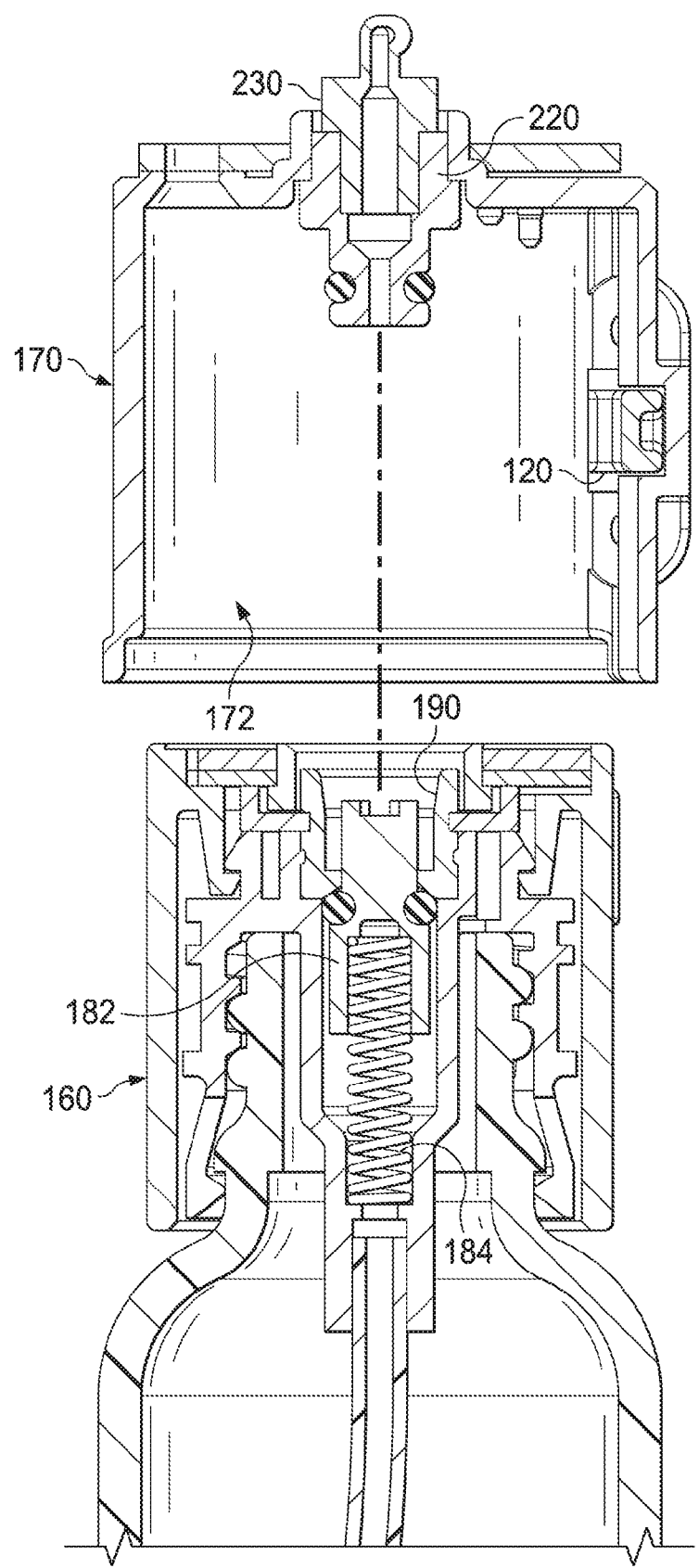
FIG. 5A is a cross-sectional view of a third member of a locking cap spaced from a second member of the locking cap according to embodiments of the present disclosure.

FIG. 5A is a cross-sectional view of the third member 170 of the locking cap 130 spaced from the second member 160 according to embodiments of the present disclosure. The third member 170 includes a cavity 172 within which the second member 160 may be received. In some embodiments, the cavity 172 is shaped so that a diameter of the cavity 172 is slightly larger than an outside diameter of the second member 160. In such embodiments, the second member 160 may fit within the cavity 172 of the third member 170 such that a fluid-tight seal is created between the second member 160 and the third member 170. In other embodiments, the cavity 172 is sized such that a gap is present between the second member 160 and the third member 170 when the second member 160 is received within the cavity 172.

In several examples, the valve 182 may transition between an open state and a closed state. When the valve 182 is in the open state, the prescribed substance is allowed to be dispensed from the housing 132 to the intended user. In some embodiments, the prescribed substance may be dispensed in response to the processor determining that a unique biometric attribute of the intended user is detected, which will be discussed in further detail below. When the valve 182 is in the closed state, the prescribed substance is prevented from being dispensed from the housing 132. In some examples, the valve 182 is in the closed state when the second member 160 is not received within the cavity 172 of the third member 170. In such examples, the valve 182 is in the open state when the second member 160 is received within the cavity 172. In some embodiments, the biasing member 184 biases the valve 182 in the closed state. However, when the second member 160 is received within the cavity 172 of the third member 170, the coupling member 220 contacts the valve 182. In some embodiments, this connection overcomes the biasing force imparted by the biasing member 184 on the valve 182. The biasing member 184 may be compressed as the valve 182 moves from the closed state to the open state. As shown in the embodiment of FIG. 5A, the second member 160 is not received within the cavity 172, and, therefore, the coupling member 220 is not in contact with the valve 182. Thus, in the embodiment shown in FIG. 5A, the valve 182 is in the closed state.

Figure 5B:
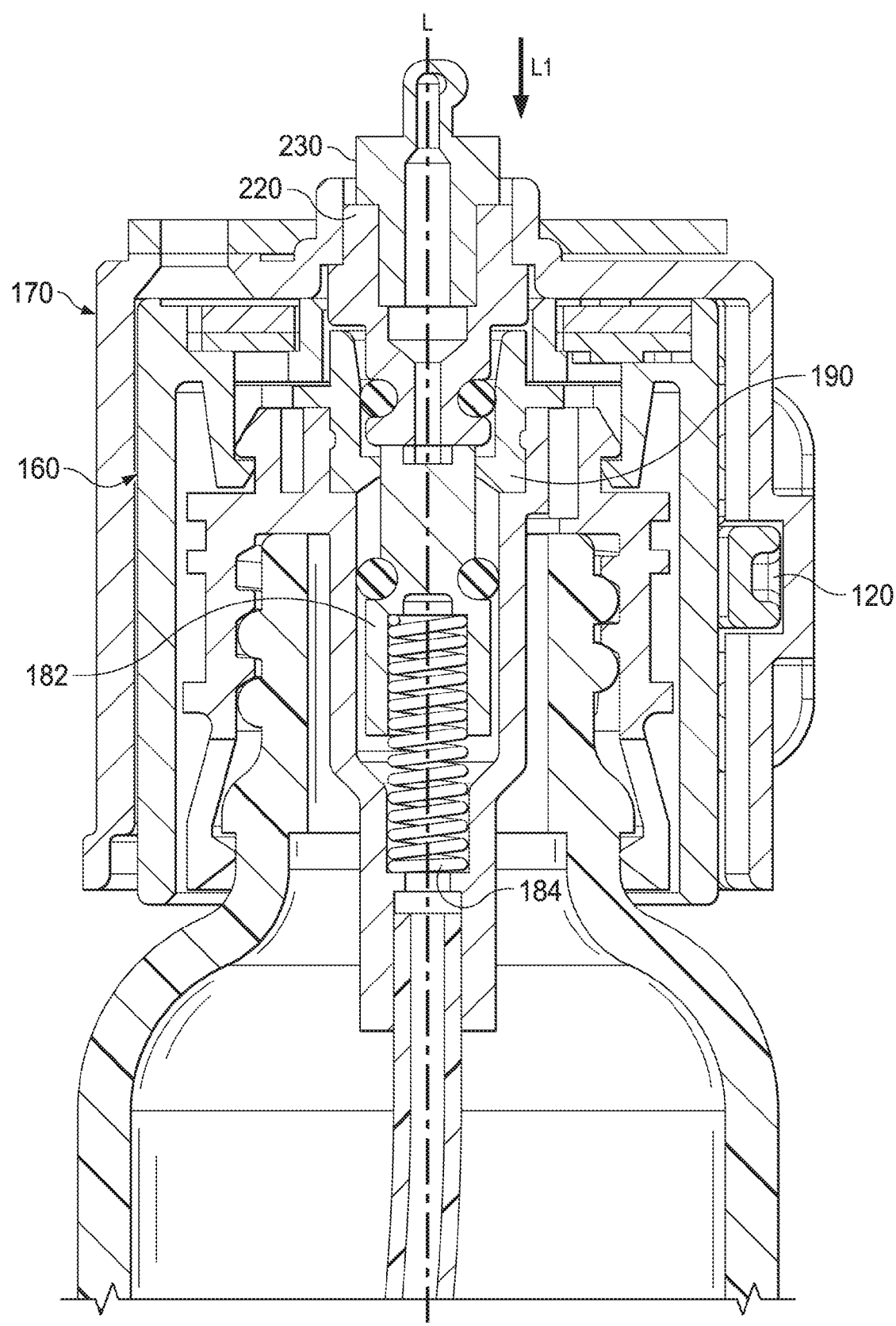
FIG. 5B is a cross-sectional view of a third member of a locking cap coupled to a second member of the locking cap according to embodiments of the present disclosure.

FIG. 5B is a cross-sectional view of the third member 170 coupled to the second member 160 according to embodiments of the present disclosure. In the embodiment shown in FIG. 5B, the second member 160 is received within the cavity 172 of the third member 170, and the valve 182 is in the open state. As can be seen, the coupling member 220 is in contact with the valve 182, and the biasing member 184 is compressed. Therefore, the valve 182 has moved in the direction L1, and the prescribed substance is able to be dispensed from the housing 132. For example, the pump 230 may cause the prescribed substance to be dispensed from the housing 132.

Figure 5C:
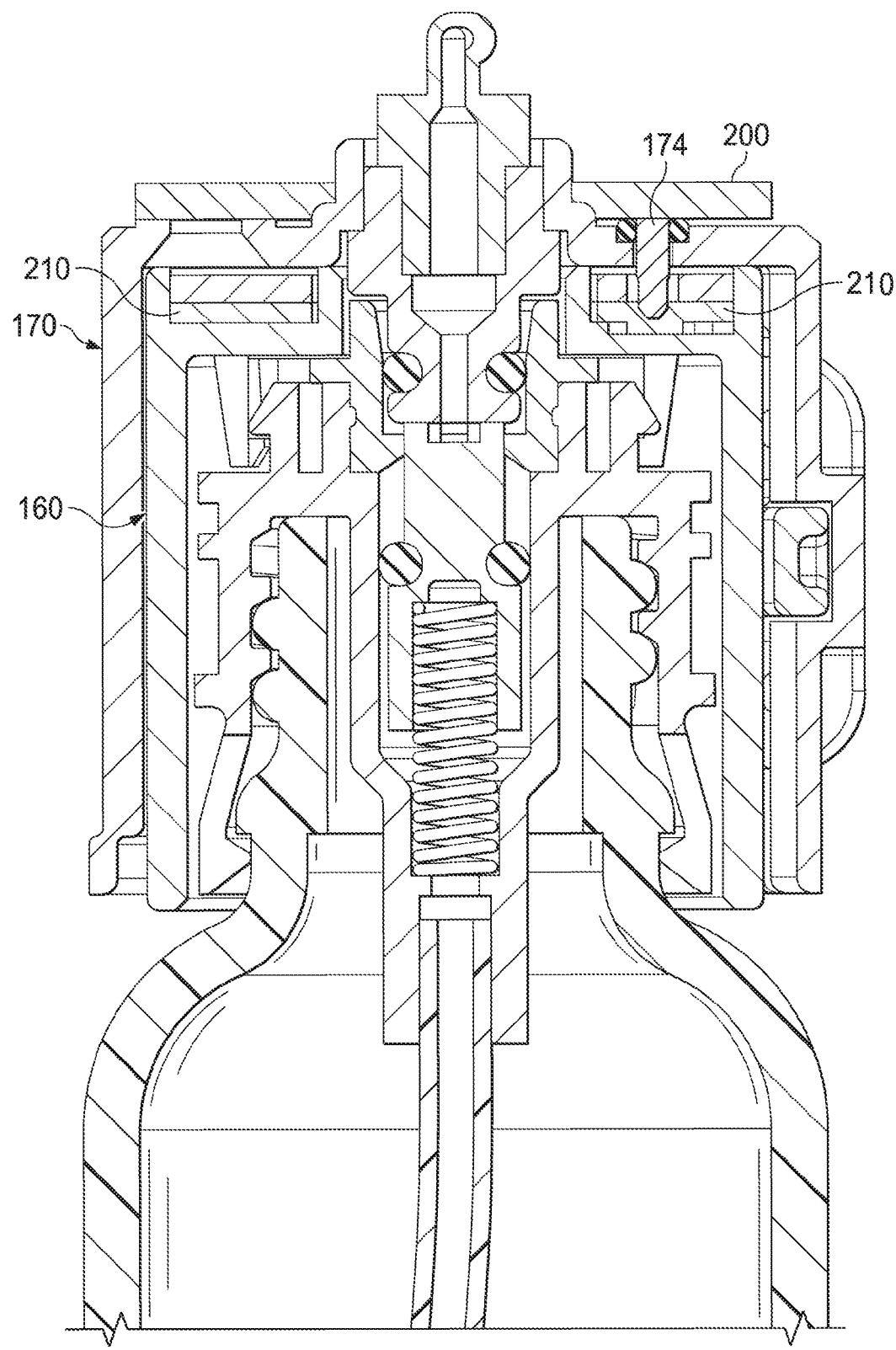
FIG. 5C is a cross-sectional view of a third member of a locking cap coupled to a second member of the locking cap according to embodiments of the present disclosure.

FIG. 5C is a cross-sectional view of the third member 170 coupled to the second member 160 according to embodiments of the present disclosure. The cross-sectional view of FIG. 5C is rotated about 15 degrees from the cross-sectional view of FIG. 5B. The third member 170 includes a contact member 174 to contact both the circuit board 200 and the circuit board 210. In several examples, the contact member 174 remains in contact with the circuit board 200 regardless of whether the second member 160 is coupled to the third member 170 or not. The contact member 174 facilitates communication between components of the circuit boards 200, 210. In some embodiments, a unique identifier associated with the intended user may be sent from a transceiver of the second member 160 to a transceiver of the third member 170. The transceiver of the second member 160 may be connected to the circuit board 210. The transceiver of the third member 170 may be connected to the circuit board 200. In some embodiments, the unique identifier may be stored in a memory. As shown in the embodiment of FIG. 5C, when the second member 160 is received within the cavity 172 of the third member 170, the contact member 174 contacts the circuit board 210.

Figure 5D:
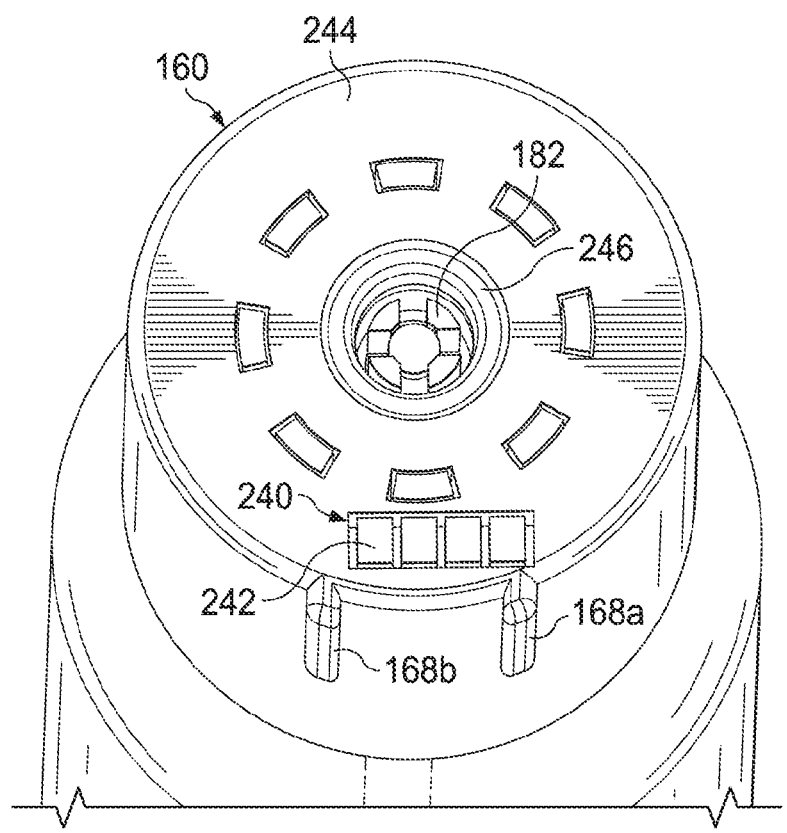
FIG. 5D is a top perspective view of a second member of a locking cap coupled to a first member of the locking cap according to embodiments of the present disclosure.

FIG. 5D is a top perspective view of the second member 160 coupled to the first member 140 according to embodiments of the present disclosure. The second member 160 includes a sensor array 240, which may include one or more sensors, positioned on a top surface 244 of the second member 160. In some embodiments, the sensor array 240 is coupled to the circuit board 210. In other embodiments, the sensor array 240 is integrated within the circuit board 210. As shown in the embodiment of FIG. 5D, the sensor array 240 includes four individual sensors 242. The sensors 242 are programmed to provide the unique identifier associated with the intended user. Thus, the second member 160 may be registered to the intended user. Therefore, in some embodiments, the intended user will only be able to access the prescribed substance within the housing 132 when the second member 160 registered to the intended user is coupled to the first member 140. In several examples, each sensor 242 is used to provide the unique identifier. In other examples, only one sensor 242 is used to provide the unique identifier. In some embodiments, though, one or more of the sensors 242 may be provided to indicate whether the third member 170 is coupled to the second member 160. In such embodiments, the one or more sensors 242 may not be included in the unique identifier associated with the intended user. It is to be understood that the sensor array 240 may include any number of sensors 242 to provide the unique identifier associated with the intended user. For example, less than four or more than four sensors 242 may be included in the sensor array 240.

As shown in the embodiment of FIG. 5D, the second member 160 further includes an opening 246 in the top surface 244. In several examples, the valve 182 fits within the opening 246. Therefore, when the second member 160 is received within the cavity 172 of the third member 170, the valve 182 may be contacted by the coupling member 220. In such embodiments, the valve 182 may be moved from the closed state to the open state. The placement of the valve 182 within the opening 246 also prevents access to the prescribed substance within the medication housing 132. For example, a user may not place a needle or other object through the opening 246 and access the prescribed substance. Accordingly, access to the prescribed substance is prevented even when the housing 132 is not coupled to the device housing 100.

The second member 160 further includes guide ribs 168*a*, 168*b*. The guide ribs 168*a*, 168*b* are sized to fit within corresponding guide channels of the third member 170 when the second member 160 is received within the cavity 172 of the third member 170. The guide ribs 168*a*, 168*b* ensure that the second member 160 and the third member 170 will be coupled in the same rotational position when the second and third members 160, 170 are coupled together. This ensures that the sensor array 240 will be aligned with a corresponding detector array 250 of the third member 170.

Figure 5E:
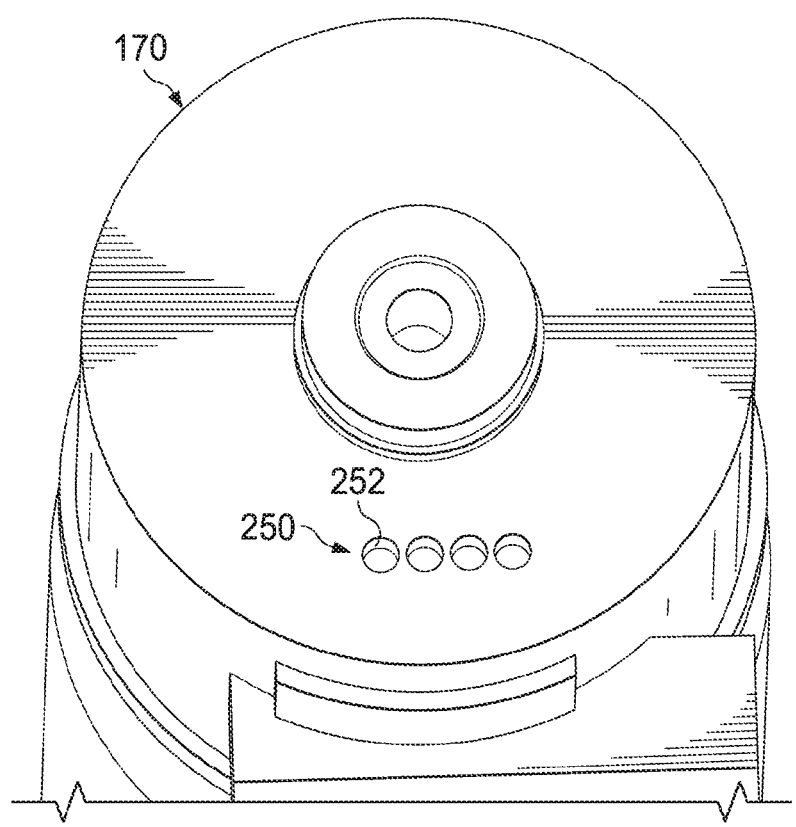
FIG. 5E is a top perspective view of a third member of a locking cap coupled to a second member of the locking cap according to embodiments of the present disclosure.

FIG. 5E is a top perspective view of the third member 170 coupled to the second member 160 according to embodiments of the present disclosure. The third member 170 includes a detector array 250, which may include one or more detectors, positioned on a bottom surface, which may be a lower surface, of the third member 170. In some embodiments, the detector array 250 is coupled to the circuit board 200. In other embodiments, the detector array 250 is integrated within the circuit board 200. As shown in the embodiment of FIG. 5E, the detector array 250 includes four individual detectors 252. The detectors 252 are positioned such that when the second member 160 is received by the third member 170, the detectors 252 align with the sensors 242 of the sensor array 240. In some embodiments, the detectors 252 are programmed to receive the unique identifier associated with the intended user from the sensors 242 of the sensor array 240. In several examples, each detector 252 is used to receive the unique identifier. In other examples, only one detector 252 is used to receive the unique identifier. In some embodiments, though, one or more of the detectors 252 may be provided to detect whether the third member 170 is coupled to the second member 160. In such embodiments, the one or more detectors 252 may not be included in the unique identifier associated with the intended user. It is to be understood that the detector array 250 may include any number of detectors 252 to receive the unique identifier of the intended user. For example, less than four or more than four detectors 252 may be included in the detector array 250. In some embodiments, the number of detectors 252 in the detector array 250 equals the number of sensors 242 in the sensor array 240.

Figure 6A:
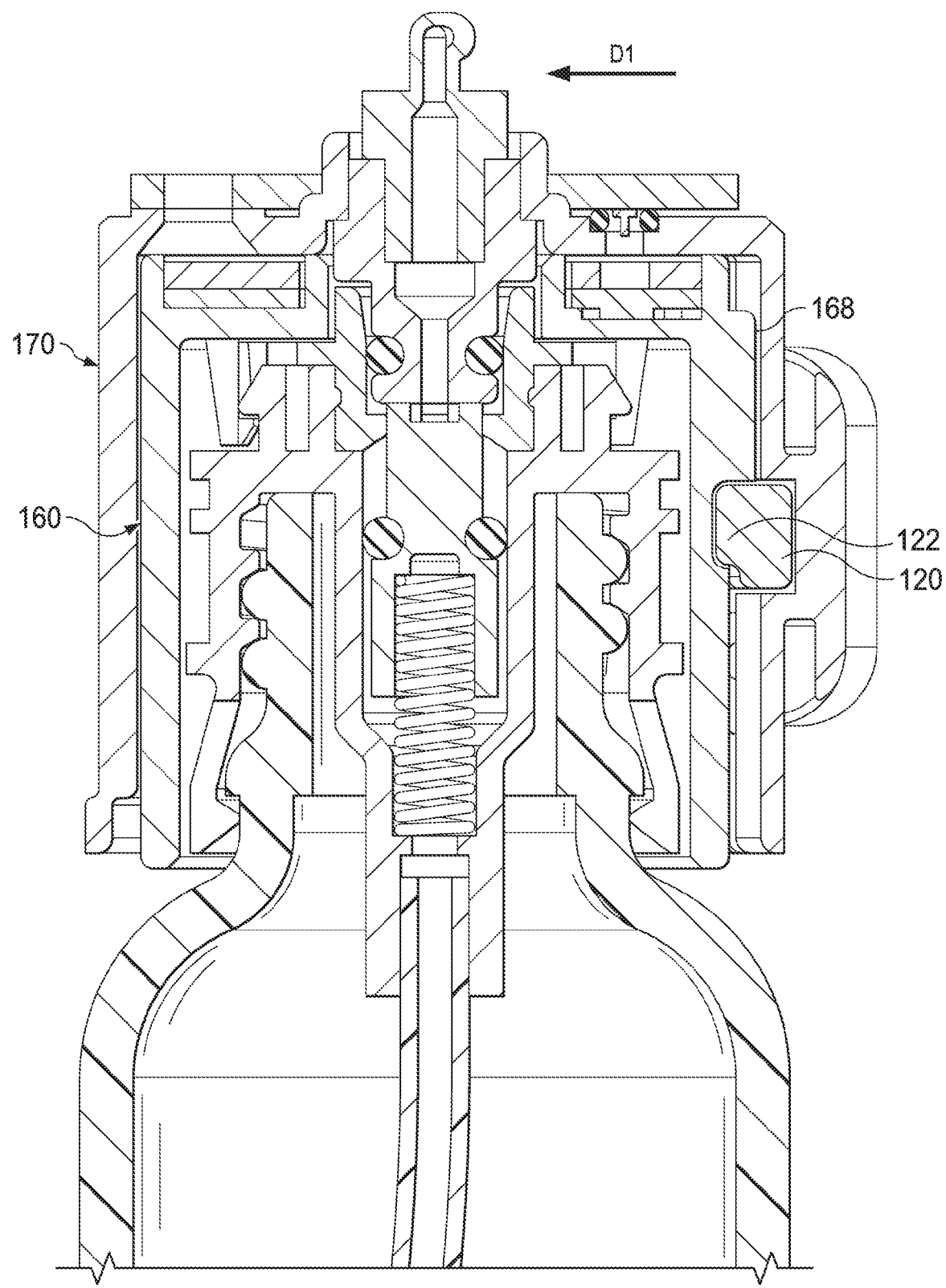
FIG. 6A is a front cross-sectional view of a release button of a third member of a locking cap when the third member is coupled to a second member of the locking cap according to embodiments of the present disclosure.

FIG. 6A is a front cross-sectional view of the release button 120 of the locking cap 130 when the third member 170 is coupled to the second member 160 according to embodiments of the present disclosure. The release button 120 includes a locking tab 122. The locking tab 122 extends in a direction DI toward the second member 160. Additionally, in some embodiments, the locking tab 122 is positioned underneath at least one of the guide ribs 168a, 168b of the second member 160. For example, the locking tab 122 may be positioned underneath the guide rib 168a and not the guide rib 168b. Therefore, when the second member 160 is received within the cavity 172 of the third member 170, the locking tab 122 prevents removal of the second member 160 from the cavity 172 until the release button 120 is depressed, which will be described in further detail below. In alternative embodiments, the locking tab 122 may be positioned underneath the guide rib 168b and not the guide rib 168a. In further examples, the locking tab 122 may be positioned underneath both guide ribs 168a, 168b.

Figure 6B:
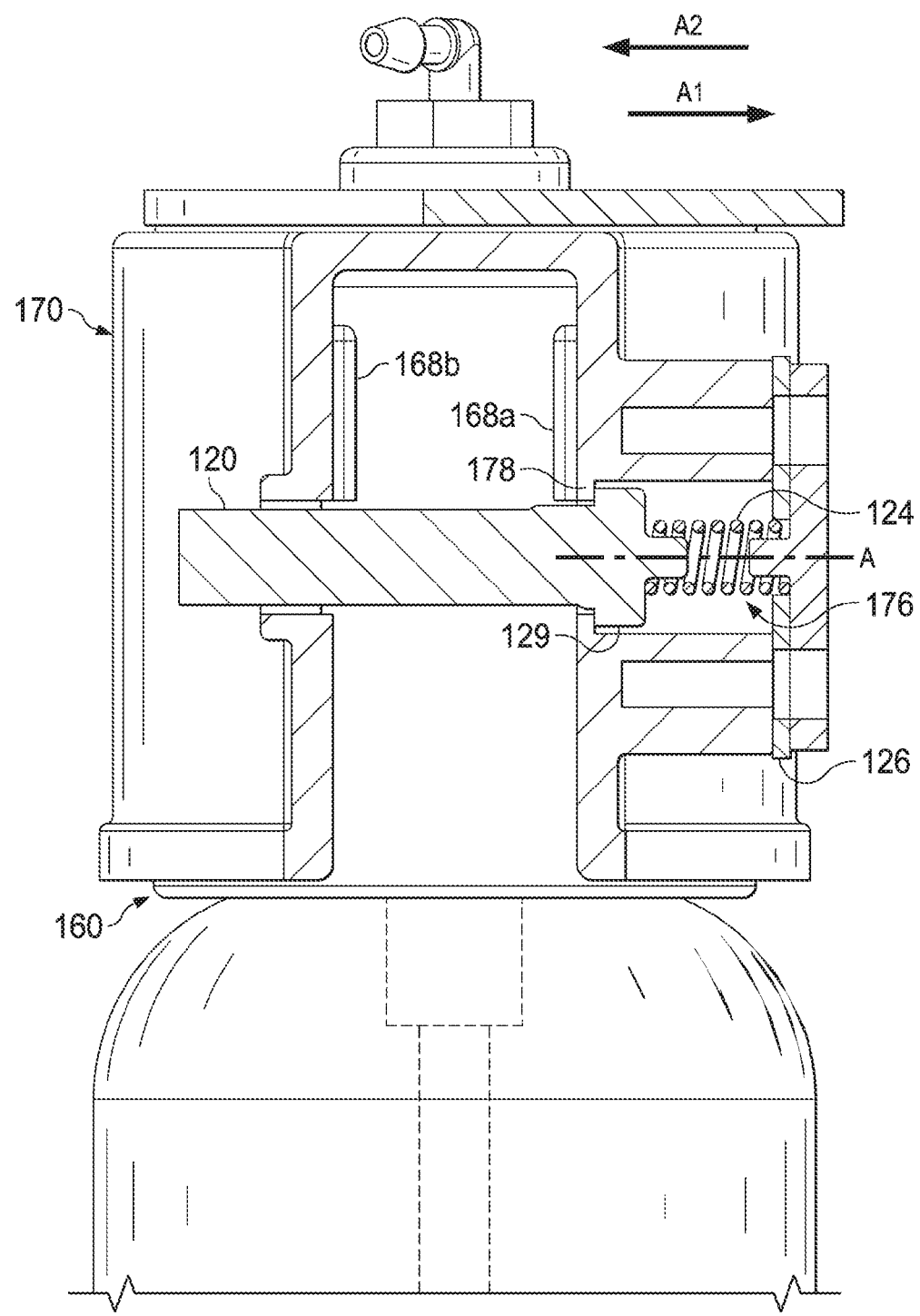
FIG. 6B is a side cross-sectional view of a release button of a third member of a locking cap when the third member is coupled to a second member of the locking cap according to embodiments of the present disclosure.

FIG. 6B is a side cross-sectional view of the release button 120 when the third member 170 is coupled to the second member 160 according to embodiments of the present disclosure. As discussed above, the release button 120, and particularly the locking tab 122, are positioned below at least one of the guide ribs 168a, 168b of the second member 160 when the second member 160 is received within the cavity 172 of the third member 170. In the embodiment shown in FIG. 6B, the locking tab 122 is positioned beneath the guide rib 168a.

As shown in the embodiment of FIG. 6B, the release button 120 further includes a proximal tab 129 and a biasing member 124. In some embodiments, the biasing member 124 is a spring. In other embodiments, the biasing member 124 may be any other suitable type of component configured to bias the release button 120 in a particular direction. In some embodiments, the third member 170 includes a sealing member 126, a cavity 176, and at least one tab 178. The sealing member 126 may provide a liquid-proof seal to prevent liquid from entering the cavity 176. A liquid-proof cavity 176 allows the release button 120 to function properly and reduces the chances of a malfunction. As will be discussed in further detail below, when the release button 120 is depressed, the biasing member 124 is compressed. This may allow the second member 160 to be removed from the cavity 172 of the third member 170. When the release button 120 is depressed, the release button 120 moves in a direction A1, which may be substantially parallel to a longitudinal axis A of the biasing member 124. In some embodiments, the biasing member 124 may bias the release button 120 in a direction A2 such that the proximal tab 129 of the release button 120 is in contact with the tab 178 of the third member 170.

Figure 6C:
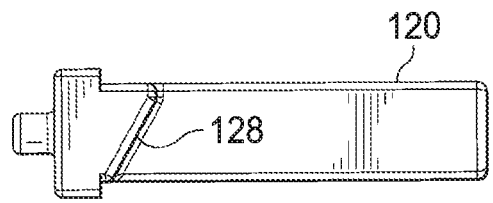
FIG. 6C is a side view of a release button of a third member of a locking cap according to embodiments of the present disclosure.

FIG. 6C is a side view of the release button 120 according to embodiments of the present disclosure. The release button 120 further includes a tapered surface 128. In some embodiments, as the second member 160 is inserted into the cavity 172 of the third member 170, the guide rib 168a, for example, contacts the tapered surface 128. As the second member 160 is inserted further into the cavity 172, the guide rib 168a rides along the tapered surface 128, which causes the release button 120 to move in the direction A1. In some examples, when the second member 160 is fully inserted in the cavity 172, the guide rib 168a clears the tapered surface 128 of the release button 120. In such examples, the guide rib 168a is positioned above the release button 120. When the guide rib 168a clears the tapered surface 128 and moves above the release button 120, the biasing member 124 moves the release button 120 back to the locking position as shown in the embodiment of FIG. 6B. In the locking position, the proximal tab 129 of the release button 120 is in contact with the tab 178 of the third member 170. The presence of the tapered surface 128 allows the second member 160 to be inserted into the cavity 172 of the third member 170 without needing to actively depress the release button 120.

Figure 6D:
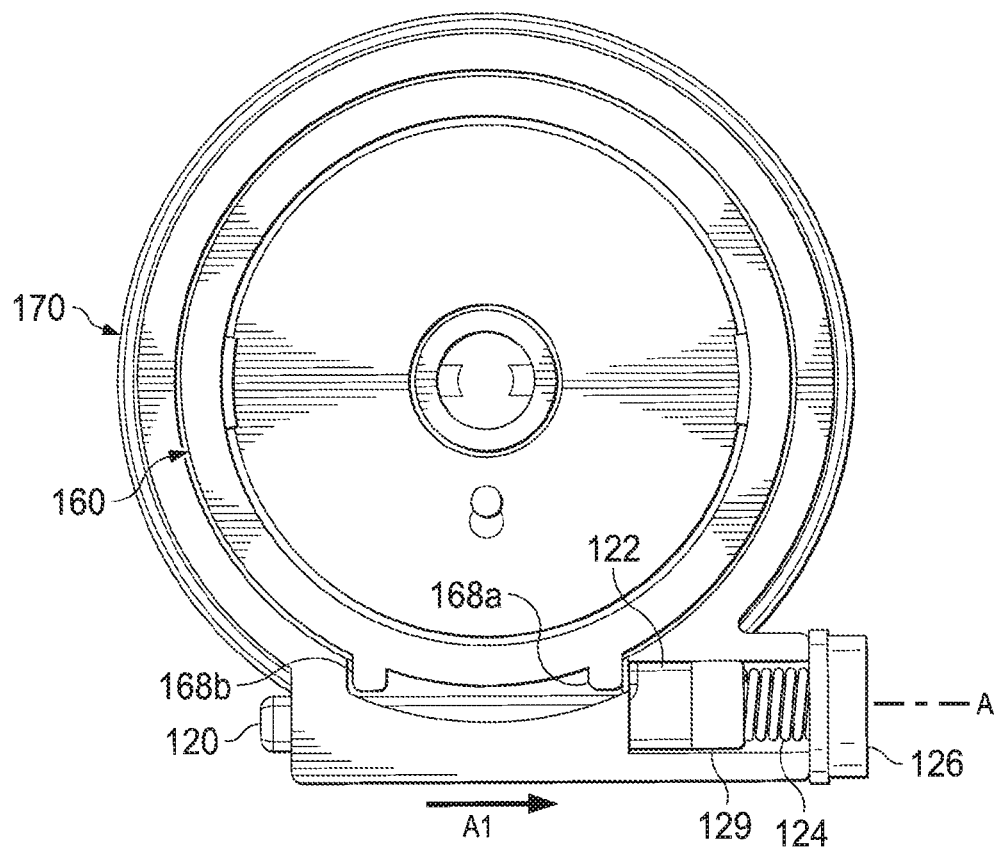
FIG. 6D is a top cross-sectional view of a release button of a third member of a locking cap when the third member is coupled to a second member of the locking cap according to embodiments of the present disclosure.

FIG. 6D is a top cross-sectional view of the release button 120 in an unlocked position according to embodiments of the present disclosure. The release button 120 is in the unlocked position when the release button 120 is depressed. When the release button 120 is depressed, the biasing member 124 is compressed. Thus, the release button 120 moves in the direction A1. As the release button 120 moves in the direction A1, the locking tab 122 moves in the direction A1. In some embodiments, when the release button 120 reaches the final, unlocked position, as shown in the embodiment of FIG. 6D, the locking tab 122 is located within the cavity 176. In such embodiments, the locking tab 122 is no longer positioned beneath the guide rib 168a. Therefore, the locking tab 122 no longer prevents removal of the second member 160 from the cavity 172. Thus, the second member 160 may be removed from the cavity 172.

Figure 7A:
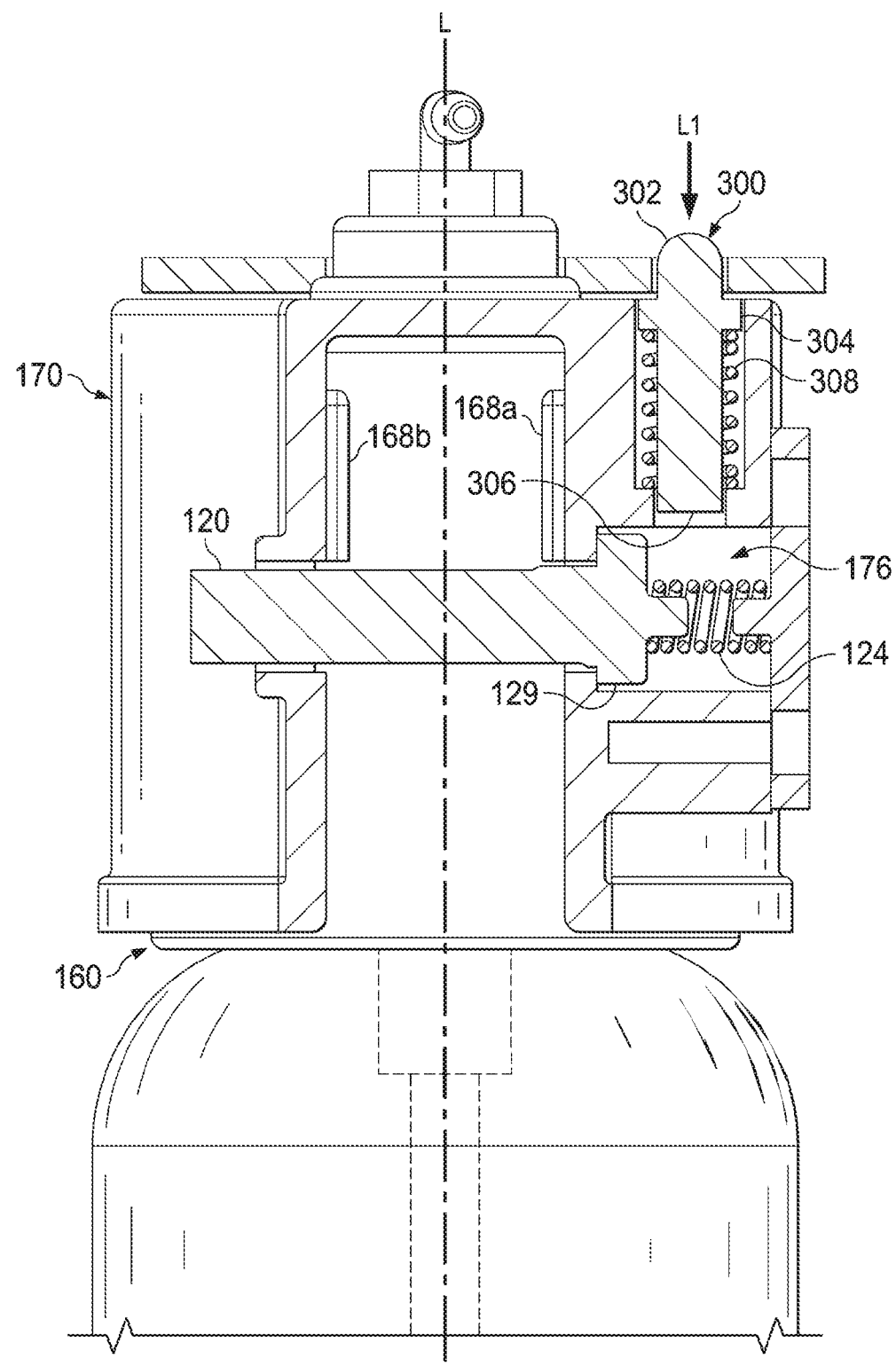
FIG. 7A is a side cross-sectional view of a stopper of a third member of a locking cap when the stopper is in an unlocked position according to embodiments of the present disclosure.

FIG. 7A is a side cross-sectional view of a stopper 300 of the third member 170 when the stopper 300 is in an unlocked position according to embodiments of the present disclosure. The stopper 300 includes a proximal portion 302, a proximal tab 304, a distal portion 306, and a biasing member 308. In some embodiments, the biasing member 308 is a spring. In other embodiments, the biasing member 308 may be any other suitable type of component configured to bias the stopper 300 in a particular direction. In some embodiments, the proximal tab 304 engages the biasing member 308 when the stopper 300 is depressed and moves in a direction L1. This may cause the biasing member 308 to compress. In some embodiments, the stopper 300 may be depressed by pushing down on the proximal portion 302. In some examples, a motor, a solenoid, a mechanical linkage, or any other suitable component, may be used to push the proximal portion 302 of the stopper 300 in the direction L1 to depress the stopper 300.

Figure 7B:
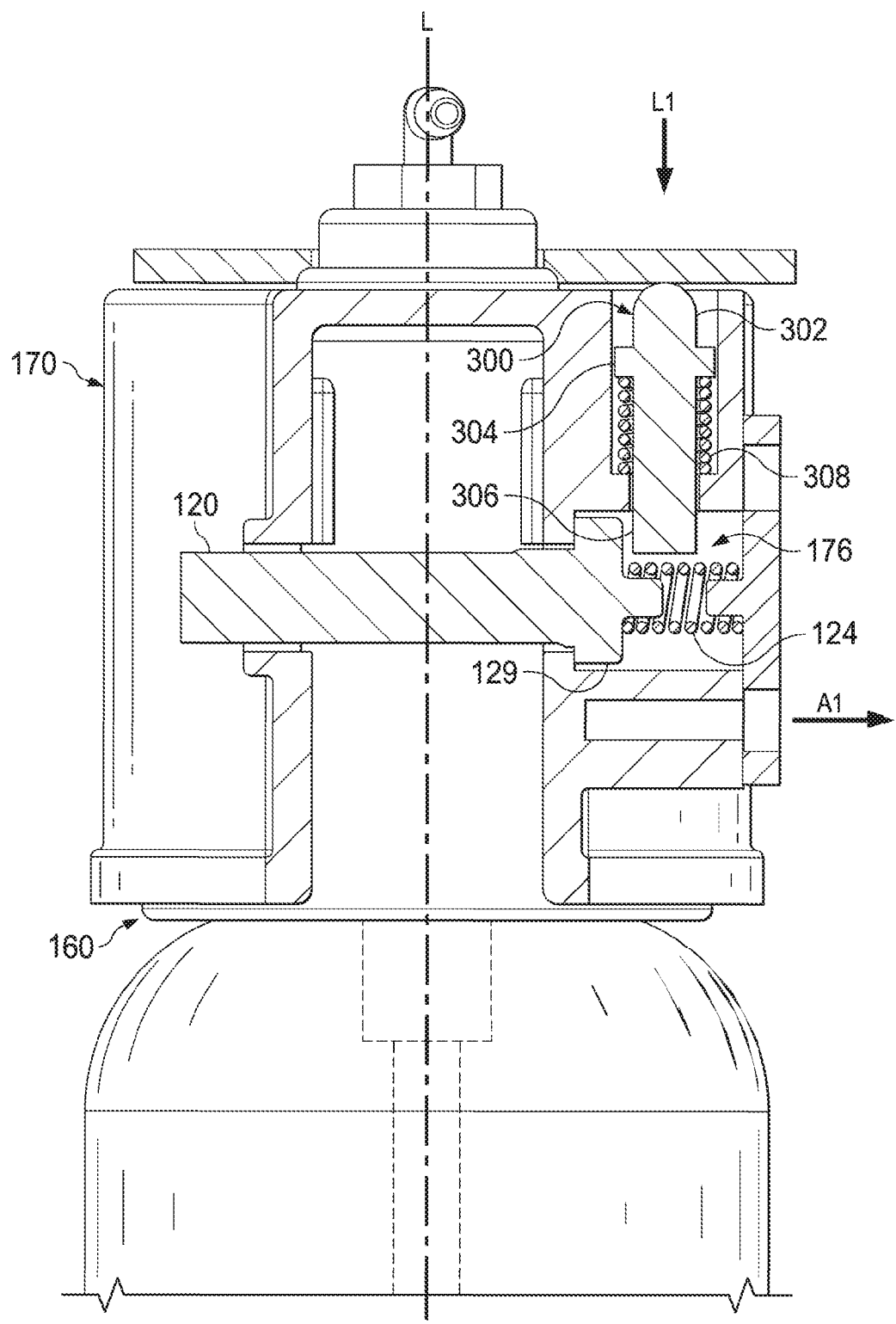
FIG. 7B is a side cross-sectional view of a stopper of a third member of a locking cap when the stopper is in a locked position according to embodiments of the present disclosure.

FIG. 7B is a side cross-sectional view of the stopper 300 of the third member 170 when the stopper 300 is in a locked position according to embodiments of the present disclosure. The stopper 300 is in the locked position when the distal portion 306 of the stopper 300 enters the cavity 176. In some embodiments, the stopper 300 may be moved to the locked position after the second member 160 is received and locked within the cavity 172 of the third member 170. In the locked position, the distal portion 306 prevents the proximal tab 129 from moving in the direction A1 because the proximal tab 129 will contact the distal portion 306 of the stopper 300. Accordingly, the locking tab 122 of the release button 120 will remain beneath the guide rib 168a. Thus, the second member 160 may be prevented from being removed from the cavity 172 of the third member 170. The stopper 300 may be moved to the locked position to prevent the release button 120 from being depressed while the prescribed substance is being dispensed from the housing 132. This helps to ensure that the prescribed substance is being correctly dispensed (e.g., in a correct dosage). This may also help prevent unauthorized access to the prescribed substance, which adds a further security measure to the locking cap 130. In several embodiments, the stopper 300 may be actively held in the locked position by the component used to depress the stopper 300. In other embodiments, the stopper 300 may be held in the locked position by a locking mechanism, such as a mechanical lock, an electromagnetic lock, etc.

Figure 8:
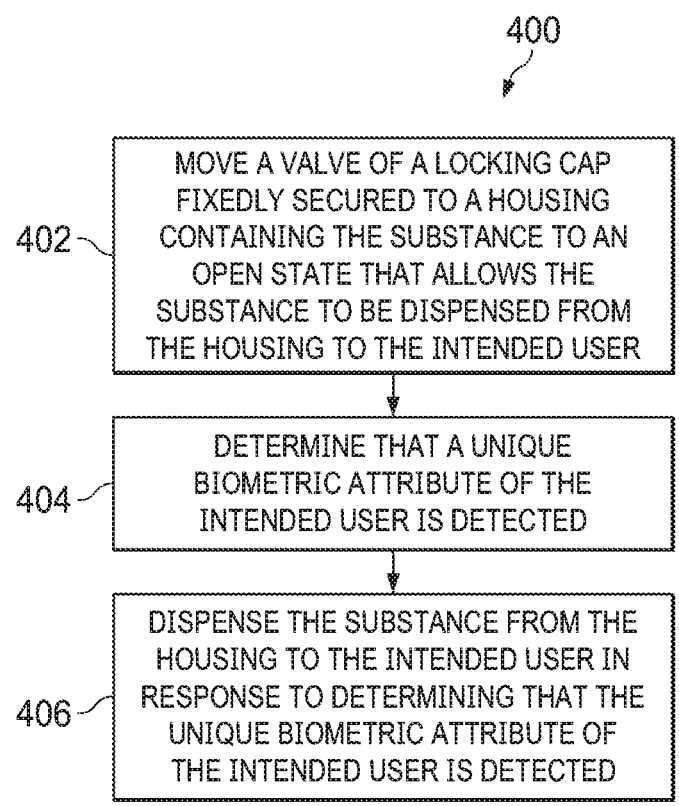
FIG. 8 is a flow diagram of a method of securely dispensing a substance to an intended user according to embodiments of the present disclosure.

FIG. 8 is a flow diagram of a method 400 of securely dispensing a substance to an intended user according to embodiments of the present disclosure. The method 400 can be better understood with reference to FIGS. 1 and 5A-E. As illustrated, the method 400 includes a number of enumerated steps, but embodiments of the method 400 may include additional steps before, after, and in between the enumerated steps. In some embodiments, one or more of the enumerated steps may be omitted or performed in a different order.

At step 402, the method 400 includes moving a valve of a locking cap fixedly secured to a housing containing the substance to an open state that allows the substance to be dispensed from the housing to the intended user. In some embodiments, the locking cap is the locking cap 130, and the housing is the housing 132. In such embodiments, the valve is the valve 182. In some examples, the method 400 may additionally include a step of fixedly securing the locking cap 130 to the housing 132. In some embodiments, fixedly securing the locking cap 130 to the housing 132 may include encasing the lip 138 of the housing 132 with the plurality of latching members 148 of the first member 140 of the locking cap 130. In other embodiments, fixedly securing the locking cap 130 to the housing 132 may include coupling the second member 160 of the locking cap 130 with the first member 140. In some examples, coupling the second member 160 to the first member 140 includes encasing the plurality of latching members 148 with the distal portion 164 of the second member 160. In several examples, moving the valve 182 to the open state comprises inserting the second member 160 into the cavity 172 of the third member 170.

At step 404, the method 400 includes determining that a unique biometric attribute of the intended user is detected. In some embodiments, the processor may determine whether the intended user's unique biometric attribute is positioned on a biometric sensor. The biometric sensor may be located on a surface of the device housing 100. For example, the processor may compare a fingerprint model associated with an input by the biometric sensor to a predetermined fingerprint model associated with the intended user to determine whether there is a match between the current user of the device housing 100 and the intended user of the device housing 100. In some instances, a user's unique biometric attribute is detected by the biometric sensor when the user's unique biometric attribute is positioned on the biometric sensor. In other examples, the user's unique biometric attribute is detected by the biometric sensor when the user's unique biometric attribute is spaced from the biometric sensor. In other embodiments, the determination includes determining that a unique dentition of the intended user is positioned within a recess of a mouthpiece (e.g., the COPA device 110). In such embodiments, this may include determining, by the processor, that the unique dentition of the intended user is positioned within the recess of the mouthpiece. In some embodiments, a capacitive sensor array may be positioned within the recess of the mouthpiece. In several embodiments, the capacitive sensor array may detect a capacitive map associated with the dentition of the current user of the mouthpiece. In some examples, the processor may compare the capacitive map associated with the current user of the mouthpiece with a predetermined capacitive map associated with the intended user. Additional details regarding the COPA device 110 may be found in U.S. patent application Ser. No. 15/958,809, filed Apr. 29, 2018, which is hereby incorporated by reference in its entirety.

At step 406, the method 400 includes dispensing the substance from the housing to the intended user in response to determining that the unique biometric attribute of the intended user is detected. In some embodiments, the dispensing includes dispensing the substance in response to determining, by the processor, that the unique dentition of the intended user is positioned within a recess of the mouthpiece. In other embodiments, the dispensing includes, separately or additionally, dispensing the substance in response to the processor determining that the unique identifier of the second member 160 associated with the intended user is detected by the detector array 250 of the third member 170. In several examples, this determination may include receiving, by the detector array 250, the unique identifier associated with the intended user. The detector array 250 may receive the unique identifier associated with the intended user from the sensor array 240 of the second member 160.

Figure 9:
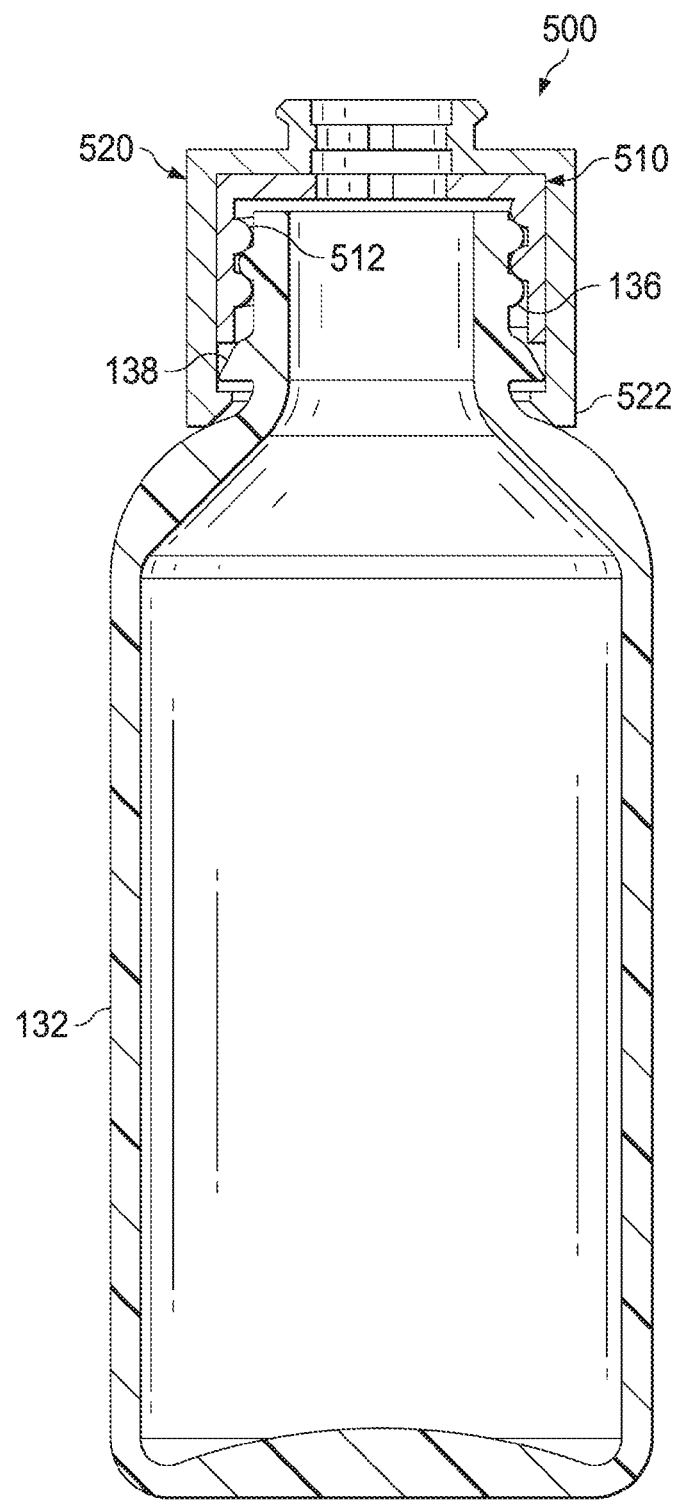
FIG. 9 is a cross-sectional view of a first member of a locking cap and a second member of the locking cap coupled to a housing according to embodiments of the present disclosure.

FIG. 9 is a cross-sectional view of a first member 510 of a locking cap 500 and a second member 520 of the locking cap 500 coupled to the housing 132 according to embodiments of the present disclosure. The discussion above with respect to FIGS. 1-8 similarly applies to the embodiment of FIG. 9. Any differences between the components discussed above and the components illustrated in the embodiment of FIG. 9 will now be discussed.

In alternative embodiments, the locking cap 500 may be received within the device housing 100 to securely dispense the prescribed substance from the housing 132. The locking cap 500 includes a first member 510 and a second member 520. The first member 510 includes grooves 512 corresponding to the threads 136 of the housing 132. The grooves 512 receive the threads 136. In this manner, the first member 510 and the housing 132 can be threadedly coupled. The second member 520 includes a lower tab 522. In some embodiments, as discussed above with respect to the locking cap 130, when the second member 520 is rotated, the first member 510 rotates together with the second member 520. Therefore, to attach the first member 510 to the housing 132, the first member 510 is placed on top of the housing 132. The second member 520 may be rotated (e.g., in a clockwise direction or in a counter-clockwise direction) to screw the first member 510 onto the housing 132. In some embodiments, the second member 520 is rotated until the lower tab 522 of the second member 520 travels over and then engages with the lip 138 of the housing 132. Therefore, the second member 520 may be fixedly secured to the housing 132 (e.g., in the axial direction). The second member 520 may then be received within the cavity 172 of the third member 170 as discussed above.

Figure 10A:
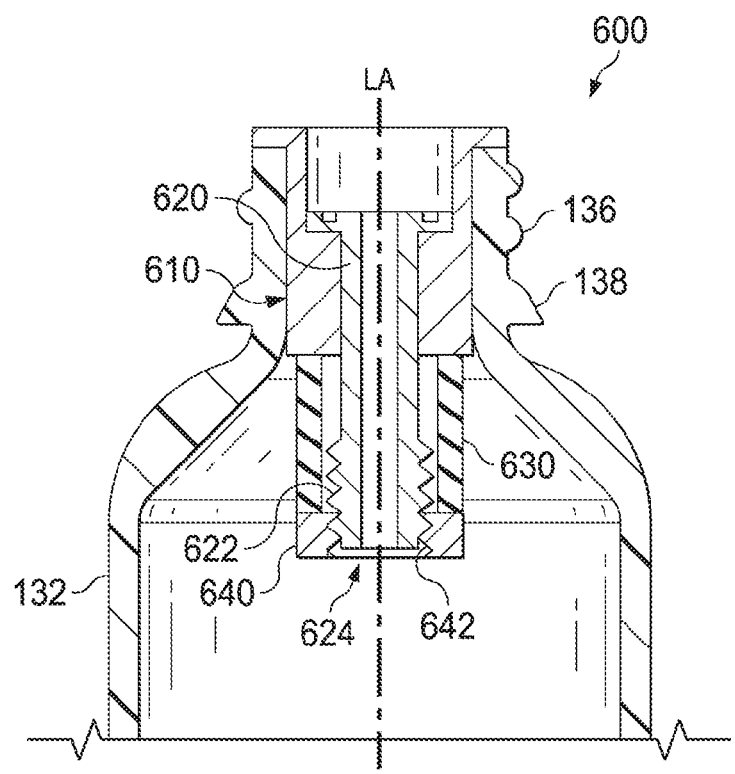
FIG. 10A is cross-sectional view of a first member of a locking cap in a non-compressed state according to embodiments of the present disclosure.

FIG. 10A is cross-sectional view of a locking cap 600 in a non-compressed state according to embodiments of the present disclosure. The discussion above with respect to FIGS. 1-8 similarly applies to the embodiments of FIGS. 10A and 10B. Any differences between the components discussed above and the components illustrated in the embodiments of FIGS. 10A and 10B will now be discussed.

In alternative embodiments, a locking cap 600 may be received within the device housing 100 to securely dispense the prescribed substance from the housing 132. The locking cap 600 includes a stopper 610, an elongate, threaded member 620, a compression member 630, and a threaded nut 640. The elongate, threaded member 620 includes threads 622 and a longitudinal axis LA. The threaded nut 640 includes grooves 642 that correspond to and receive the threads 622. Accordingly, the elongate, threaded member 620 and the threaded nut 640 are threadedly engageable. In some embodiments, the compression member 630 can transition between a non-compressed state and a compressed state. When the compression member 630 is in the non-compressed state, as shown in the embodiment of FIG. 10A, the locking cap 600 is capable of being inserted into and removed from the housing 132. In some embodiments, to transition the compression member 630 from the non-compressed state to the compressed state, the threaded nut 640 is rotated about the longitudinal axis LA.

Figure 10B:
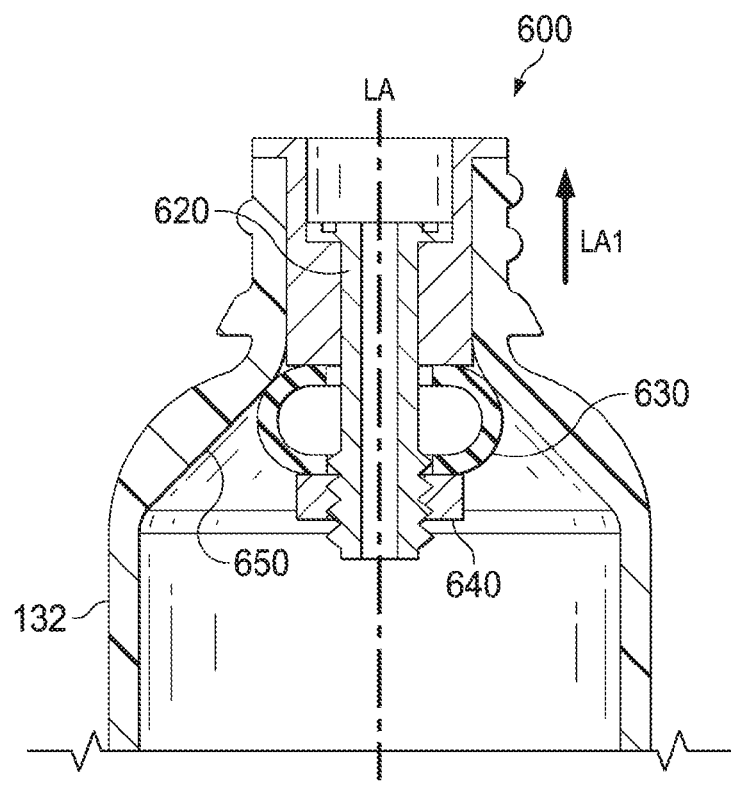
FIG. 10B is cross-sectional view of a first member of a locking cap in a compressed state according to embodiments of the present disclosure.

FIG. 10B is cross-sectional view of the locking cap 600 in a compressed state according to embodiments of the present disclosure. When the threaded nut 640 is rotated, the threaded nut 640 moves up the elongate, threaded member 620 in a direction LA1, which is substantially parallel to the longitudinal axis LA. As the threaded nut 640 moves in the direction LA1, the compression member 630 compresses until the compression member 630 rests against an inner surface 650 of the housing 132. In several examples, the interaction between the compression member 630 and the inner surface 650 of the housing 132 creates a seal preventing the locking cap 600 from being removed from the housing 132. In some embodiments, the locking cap 600 may then be received within the third member 170. In other embodiments, the second member 160 may be placed over the locking cap 600. In such embodiments, the second member 160 may encase the housing 132. Then, in such embodiments, the second member 160 may be received by the third member 170.

Figure 11A:
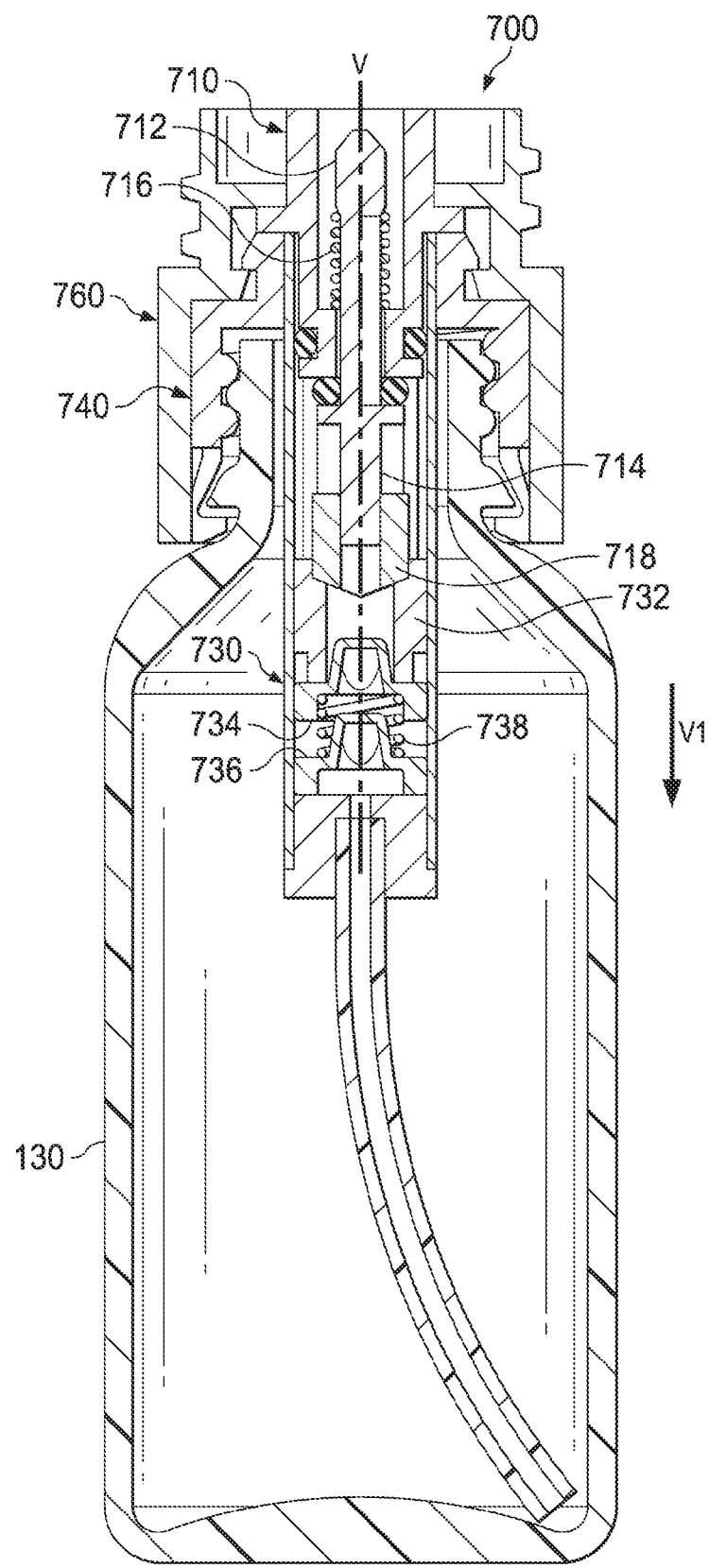
FIG. 11A is a side cross-sectional view of a first member of a locking cap coupled to a housing including a pump assembly and a second member of the locking cap coupled to the first member according to embodiments of the present disclosure.

FIG. 11A is a side cross-sectional view of a first member 740 coupled to the housing 132 including a pump assembly 730 and a second member 760 coupled to the first member 740 according to embodiments of the present disclosure. The discussion above with respect to FIGS. 1-8 similarly applies to the embodiments of FIGS. 11A and 11B. Any differences between the components discussed above and the components illustrated in the embodiments of FIGS. 11A and 11B will now be discussed.

In alternative embodiments, a locking cap 700 includes the first member 740, the second member 760, a valve 710, and the pump assembly 730. The valve 710 includes a longitudinal axis V, a valve stem 712, a shaft 714, a biasing member 716, and a cam 718. The pump assembly 730 includes a cam follower 732, an upper member 734, a lower member 736, and a biasing member 738. Therefore, as shown in the embodiment of FIG. 11A, the housing 132 includes both a valve (e.g., the valve 710) and a pump (e.g., the pump assembly 730). In some embodiments, it may be beneficial to include both a valve and a pump within the housing 132 because after a dosage of the prescribed substance has been dispensed during a pump cycle, any residual amount of the prescribed substance remaining in the fluid pathway will be contained within the housing 132. If the pump assembly 730, for example, were to be included outside of the housing 132, after a dosage of the prescribed substance has been dispensed during a pump cycle, a residual amount of the prescribed substance may remain outside of the housing 132 (e.g., within the pump assembly 730).

In some embodiments, the first member 740 serves the same function as the first member 140. Additionally, the structure of the first member 740 may be the same structure as the first member 140. In other embodiments, the structure of the first member 740 may be a different structure than the first member 140. In some embodiments, the second member 760 serves the same function as the second member 160. Additionally, the structure of the second member 760 may be the same structure as the second member 160. In other embodiments, the structure of the second member 760 may be a different structure than the second member 160.

In some examples, the biasing member 716 biases the valve 710 in a closed position, which may be a position where the prescribed substance is prevented from being dispensed from the housing 132. In some embodiments, the biasing member 716 is a spring. In other embodiments, the biasing member 716 may be any other suitable type of component configured to bias the valve 710 in a particular direction. The valve stem 712 is sized and shaped to be engaged by a third member 770, which will be discussed in further detail below. The shaft 714 is configured to move freely into and out of the cam 718. In the embodiment shown in FIG. 11A, when the valve stem 712 is pushed in a direction V1, which may be substantially parallel to the longitudinal axis V, the biasing member 716 is compressed. Thus, the valve 710 is moved from the closed position to the open position. However, merely pushing on the valve stem 712 in the direction V1 does not cause the prescribed substance to be dispensed from the housing 132. While pushing on the valve stem 712 in the direction V1 opens the valve 710, the prescribed substance is not dispensed unless and until the valve 710 is also rotated, which will be discussed in further detail below.

Figure 11B:
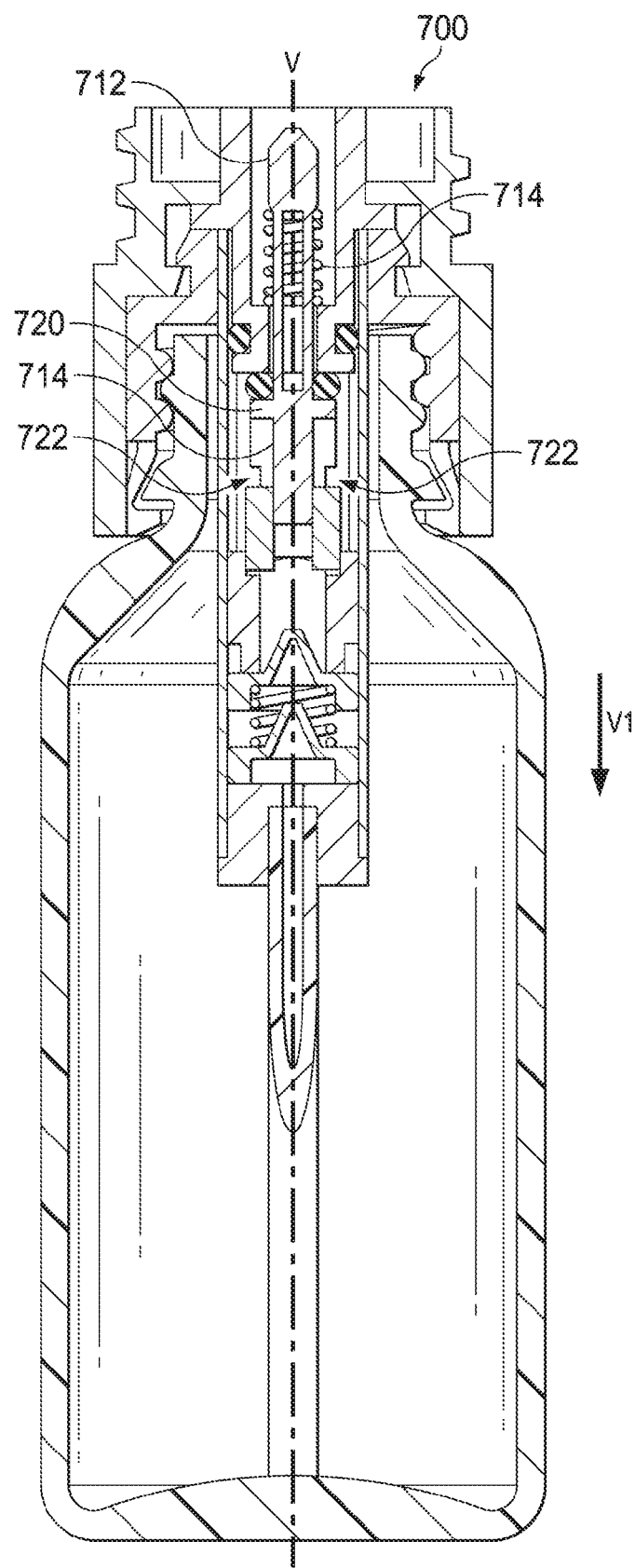
FIG. 11B is a front cross-sectional view of a first member of a locking cap coupled to a housing including a pump assembly and a second member of the locking cap coupled to the first member according to embodiments of the present disclosure.

FIG. 11B is a front cross-sectional view of the first member 740 of the locking cap 700 coupled to the housing 132 and the second member 760 of the locking cap 700 coupled to the first member 740 according to embodiments of the present disclosure. The valve 710 further includes a stopping member 720 and a plurality of tabs 722. In some embodiments, the tabs 722 mark a lower limit of vertical travel for the shaft 714. For example, as the shaft 714 travels in the direction V1, the stopping member 720 of the valve 710 contacts the tabs 722 and stops the vertical motion of the shaft 714. In several embodiments, the tabs 722 stop the vertical motion of the shaft 714 before the shaft 714 would cause the pump assembly 730 to open and start dispensing the prescribed substance from the housing 132.

Figure 12A:
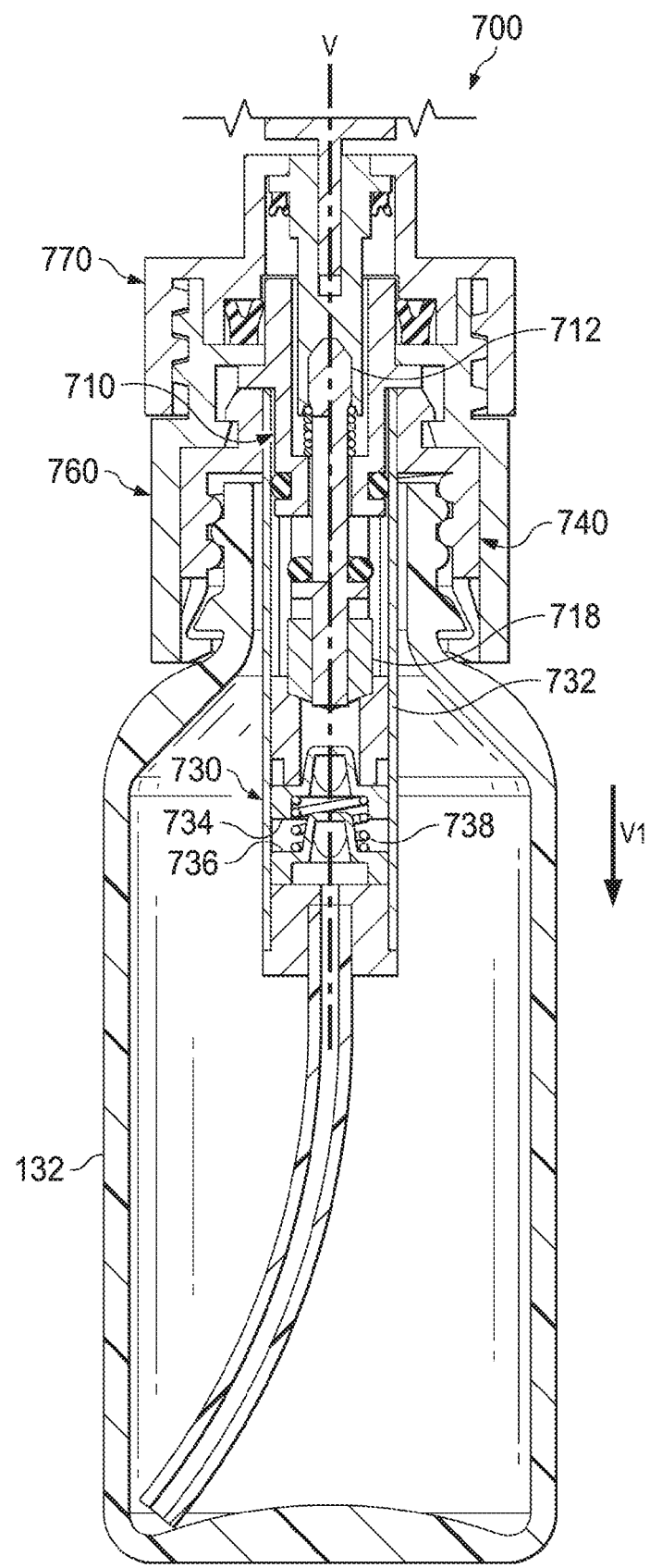
FIG. 12A is a side cross-sectional view of a locking cap coupled to a housing including a pump assembly in a non-compressed state according to embodiments of the present disclosure.
Figure 12B:
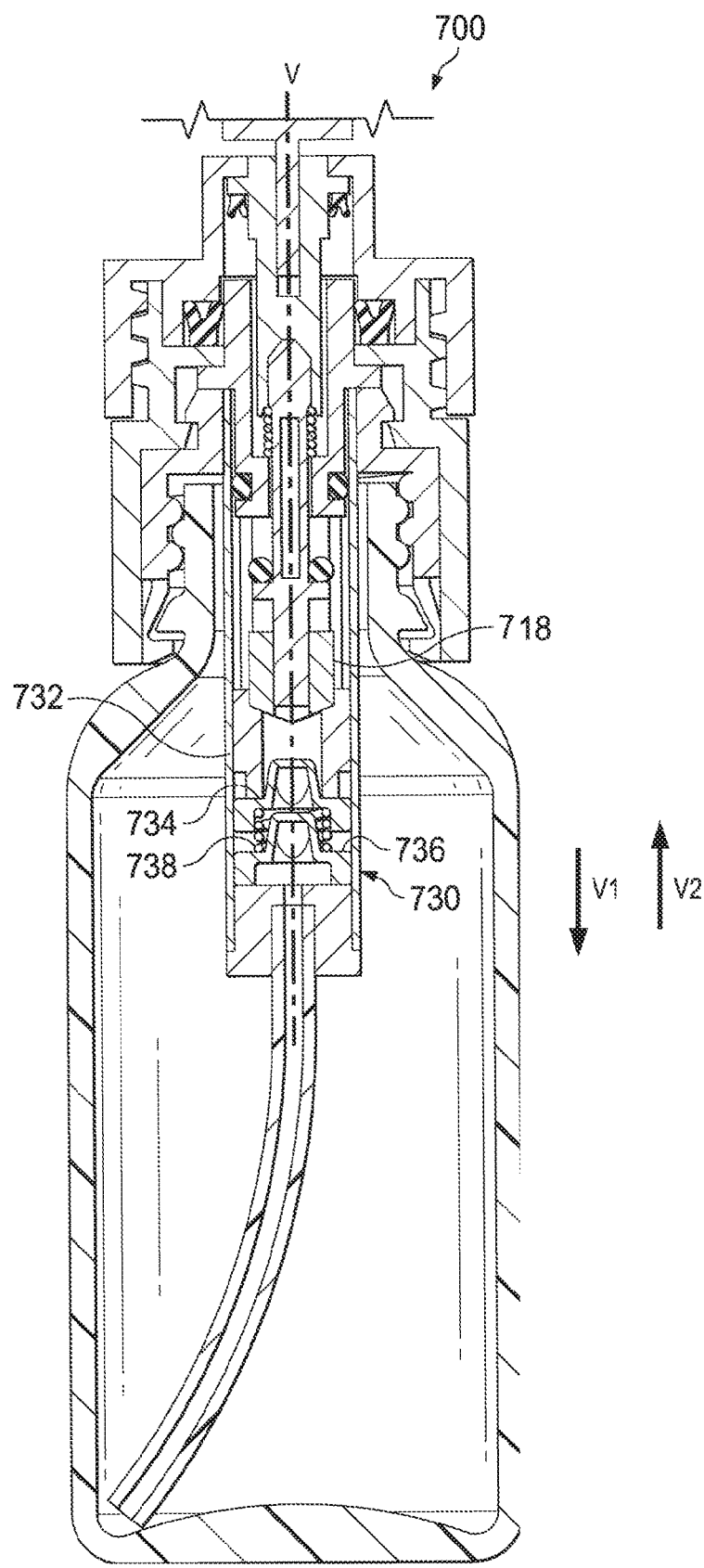
FIG. 12B is a side cross-sectional view of a locking cap coupled to a housing including a pump assembly in a compressed state according to embodiments of the present disclosure.

FIG. 12A is a side cross-sectional view of the locking cap 700 including the pump assembly 730 in a non-compressed state according to embodiments of the present disclosure. FIG. 12B is a side cross-sectional view of the locking cap 700 coupled to the housing 132 including the pump assembly 730 in a compressed state according to embodiments of the present disclosure. In the embodiment of FIG. 12A, the second member 760 is received within the cavity 172 of a third member 770. In this embodiment, the third member 770 engages the valve stem 712. For example, the coupling member 220 may engage the valve stem 712. In several embodiments, when the third member 770 engages the valve stem 712, the third member 770 causes the valve 710 to move from the closed position to the open position. In some embodiments, the third member 770 serves the same function as the third member 170. Additionally, the structure of the third member 770 may be the same structure as the third member 170. In other embodiments, the structure of the third member 770 may be a different structure than the third member 170.

As discussed above, to dispense the prescribed substance from the housing 132, the valve 710 can be moved to the open position and also rotated. In some embodiments, the valve 710 may be rotated by rotating the third member 770. This rotation may cause the coupling member 220 to rotate. The valve 710 may then correspondingly rotate with the coupling member 220. In some embodiments, when the valve 710 is rotated, the shaft 714 rotates the cam 718. When the cam 718 rotates, the cam follower 732 of the pump assembly 730 also rotates. The cam follower 732 may ride against and be pushed in the direction V1 by the cam 718. As the cam follower 732 moves in the direction V1, the cam follower 732 causes the upper member 734 to move towards the lower member 736. This may compress the biasing member 738. In several examples, when the biasing member 738 is compressed, the pump assembly 730 transitions from a closed position to an open position. In the open position, the pump assembly 730 may dispense the prescribed substance from the housing 132. The biasing member 738 may bias the upper member 734 in a direction V2 such that the pump assembly 730 remains in the closed position until the biasing member 738 is compressed. In some embodiments, the biasing member 738 is a spring. In other embodiments, the biasing member 738 may be any other suitable type of component configured to bias the upper member 734 in a particular direction. In several embodiments, when the valve 710 is in the open position and the pump assembly 730 is also in the open position, the prescribed substance is capable of being dispensed from the housing 132. In such embodiments, the prescribed substance may be dispensed from the housing 132 to the intended user.

The following table lists reference numerals and corresponding reference names:

TABLE 1

Reference Numerals and Corresponding Reference Names.

| Reference Numerals | Reference Names |
|---|---|
| 100 | device housing |
| 110 | COPA device |
| 120 | release button |
| 122 | locking tab |
| 124 | biasing member |
| 126 | sealing member |
| 128 | tapered surface |
| 129 | proximal tab |
| 130 | locking cap |
| 132 | medication housing |
| 134 | dip tube |
| 136 | threads |
| 138 | lip |
| 140 | first member |
| 142 | grooves |
| 144 | upper rim |
| 146 | lower rim |
| 148 | latching members |
| 150 | tab |
| 152 | recess |
| 154 | ledge |
| 155 | main body |
| 156 | upper tab |
| 157 | upper lip |
| 158 | locking groove |
| 159 | lower lip |
| 160 | second member |
| 162 | upper tab |
| 164 | distal portion |
| 166 | locking tabs |
| 168a | guide rib |
| 168b | guide rib |
| 170 | third member |
| 172 | cavity |
| 174 | contact member |
| 176 | cavity |
| 178 | tab |
| 180 | valve assembly |
| 182 | valve |
| 184 | biasing member |
| 190 | fluid connector |
| 200 | circuit board |
| 210 | circuit board |
| 220 | coupling member |
| 230 | pump |
| 240 | sensor array |
| 242 | sensors |
| 244 | top surface |
| 246 | opening |
| 250 | detector array |
| 252 | detectors |
| 300 | stopper |
| 302 | proximal portion |
| 304 | proximal tab |
| 306 | distal portion |
| 308 | biasing member |
| 400 | method |
| 402 | step |
| 404 | step |
| 406 | step |
| 500 | locking cap |
| 510 | first member |
| 512 | grooves |
| 520 | second member |
| 522 | tab |
| 600 | locking cap |
| 610 | stopper |
| 620 | member |
| 622 | threads |
| 630 | compression member |
| 640 | nut |
| 642 | grooves |
| 650 | inner surface |
| 700 | locking cap |
| 710 | valve |
| 712 | valve stem |
| 714 | shaft |
| 716 | biasing member |

TABLE 1-continued

Reference Numerals and Corresponding Reference Names.

| Reference Numerals | Reference Names |
| --- | --- |
| 718 | cam |
| 720 | stopping member |
| 722 | tabs |
| 730 | pump assembly |
| 732 | cam follower |
| 734 | upper member |
| 736 | member |
| 738 | biasing member |
| 740 | first member |
| 760 | second member |
| 770 | third member |

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A member for securely dispensing a substance to an intended user, the member comprising:
   a first member configured to threadedly engage with a housing containing the substance;
   a second member coupled to the first member, the second member configured to fixedly secure the first member to the housing;
   a third member including a cavity sized and shaped to selectively receive the second member; and
   a valve coupled to the first member such that:
      when the second member is received within the cavity of the third member, the valve is in an open state that allows the substance to be dispensed from the housing to the intended user in response to a processor determining that a unique biometric attribute of the intended user is detected, and
      when the second member is not received within the cavity of the third member, the valve is in a closed state that prevents the substance from being dispensed from the housing.

2. The member of claim 1, further comprising:
   a biasing member configured to bias the valve to the closed state when the second member is not received within the cavity of the third member.

3. The member of claim 2, wherein when the second member is received within the cavity of the third member, the biasing member is compressed.

4. The member of claim 1, wherein the first member comprises a plurality of latching members configured to encase a lip of the housing, the plurality of latching members configured to prevent removal of the first member from the housing in an axial direction.

5. The member of claim 4, wherein the second member includes a distal portion configured to encase the plurality of latching members to prevent removal of the plurality of latching members from the lip of the housing in a radial direction.

6. The member of claim 5, wherein the plurality of latching members are circumferentially arranged around a circumference of the first member.

7. The member of claim 1, wherein the first member comprises at least one proximal latching member.

8. The member of claim 7, wherein the second member comprises at least one latch configured to engage with the at least one proximal latching member of the first member to prevent removal of the second member from the first member in an axial direction.

9. The member of claim 1, wherein the valve includes a longitudinal axis, and wherein the second member is configured to rotate about the longitudinal axis of the valve when the second member is coupled to the first member.

10. The member of claim 1, wherein the unique biometric attribute comprises a unique dentition of the intended user.

11. The member of claim 10, further comprising:
    a mouthpiece having a sensor array, wherein the substance is dispensed from the housing to a mouth of the intended user through the mouthpiece.

12. The member of claim 11, wherein the processor is configured to determine that the unique biometric attribute of the intended user is detected by the sensor array.

13. The member of claim 11, wherein the sensor array is a capacitive sensor array.

14. The member of claim 13, wherein data obtained by the capacitive sensor array includes a capacitive map associated with the intended user.

15. The member of claim 14, wherein determining that the unique biometric attribute of the intended user is detected by the sensor array comprises comparing the capacitive map associated with the intended user to a predetermined capacitive map associated with the intended user.

16. The member of claim 1, wherein the second member comprises one or more sensors positioned on an upper surface of the second member, the one or more sensors configured to provide a unique identifier associated with the intended user.

17. The member of claim 16, wherein the third member comprises one or more detectors positioned on a lower surface of the third member, the one or more detectors configured to be in contact with the one or more sensors of the second member when the second member is received within the cavity of the third member.

18. The member of claim 17, wherein the one or more detectors of the third member are configured to communicate with the one or more sensors of the second member to receive the unique identifier associated with the intended user.

19. The member of claim 18, wherein the processor is further configured to cause the substance to be dispensed from the housing to a mouth of the intended user in response to determining that the one or more detectors received the unique identifier associated with the intended user.

20. A system for securely dispensing a substance to an intended user, the system comprising:
    a device housing;
    a locking cap coupled to the device housing, the locking cap comprising:
        a first member configured to threadedly engage with a housing containing the substance;
        a second member coupled to the first member, the second member configured to fixedly secure the first member to the housing;

a third member including a cavity sized and shaped to selectively receive the second member; and a valve coupled to the first member such that:
when the second member is received within the cavity of the third member, the valve is in an open state that allows the substance to be dispensed from the housing; and
when the second member is not received within the cavity of the third member, the valve is in a closed state that prevents the substance from being dispensed from the housing;

a mouthpiece coupled to the device housing, the mouthpiece including a recess; and a processor configured to:
determine that a unique dentition of the intended user is positioned within the recess of the mouthpiece; and
cause the substance to be dispensed from the housing to a mouth of the intended user in response to determining that the unique dentition of the intended user is positioned within the recess of the mouthpiece.

21. The system of claim 20, wherein the mouthpiece includes a capacitive sensor array configured to obtain data regarding dentition positioned within the recess of the mouthpiece.

22. The system of claim 21, wherein the data obtained by the capacitive sensor array includes a capacitive map associated with the intended user.

23. The system of claim 20, wherein the processor is further configured to:
compare a capacitive map associated with a user of the mouthpiece to a predetermined capacitive map associated with the intended user.

24. The system of claim 20, wherein the locking cap further comprises a biasing member configured to bias the valve to the closed state when the second member is not received within the cavity of the third member.

25. The system of claim 20, wherein the first member of the locking cap comprises a plurality of latching members configured to encase a lip of the device housing, the plurality of latching members configured to prevent removal of the first member from the device housing in an axial direction.

26. The system of claim 25, wherein the second member of the locking cap comprises a distal portion configured to encase the plurality of latching members to prevent removal of the plurality of latching members from the lip of the device housing in a radial direction.

27. The system of claim 20, wherein the second member of the locking cap comprises one or more sensors positioned on an upper surface of the second member, the one or more sensors configured to provide a unique identifier associated with the intended user.

28. The system of claim 27, wherein the third member of the locking cap comprises one or more detectors positioned on a lower surface of the third member, the one or more detectors configured to be in contact with the one or more sensors of the second member when the second member is received within the cavity of the third member.

29. The system of claim 28, wherein the one or more detectors of the third member are configured to communicate with the one or more sensors of the second member to receive a unique identifier associated with the intended user.

30. The system of claim 29, wherein the processor is further configured to cause the substance to be dispensed from the housing to the mouth of the intended user in response to determining that the one or more detectors received the unique identifier associated with the intended user.

\* \* \* \* \*